US008883750B2

(12) United States Patent
Wolff et al.

(10) Patent No.: US 8,883,750 B2
(45) Date of Patent: *Nov. 11, 2014

(54) METHOD OF TREATING DIABETES

(71) Applicant: Gilead Sciences, Inc., Foster City, CA (US)

(72) Inventors: Andrew A. Wolff, Foster City, CA (US); Markus Jerling, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/655,252

(22) Filed: Oct. 18, 2012

(65) Prior Publication Data
US 2013/0102555 A1    Apr. 25, 2013

Related U.S. Application Data

(63) Continuation of application No. 12/755,931, filed on Apr. 7, 2010, now Pat. No. 8,314,104, which is a continuation of application No. 10/443,314, filed on May 21, 2003, now abandoned.

(60) Provisional application No. 60/382,781, filed on May 21, 2002, provisional application No. 60/459,332, filed on Mar. 31, 2003.

(51) Int. Cl.
*A61K 45/06* (2006.01)
*A61K 31/495* (2006.01)
*A61K 9/00* (2006.01)
*A61K 9/48* (2006.01)
*A61K 9/20* (2006.01)
*A61K 9/02* (2006.01)

(52) U.S. Cl.
CPC ......... *A61K 45/06* (2013.01); *A61K 9/0095* (2013.01); *A61K 9/0019* (2013.01); *A61K 9/4866* (2013.01); *A61K 9/0075* (2013.01); *A61K 9/2027* (2013.01); *A61K 9/02* (2013.01); *A61K 9/2054* (2013.01); *A61K 31/495* (2013.01); *A61K 9/0014* (2013.01)
USPC .................. 514/42; 514/252.12; 514/222.5

(58) Field of Classification Search
USPC .................... 514/42, 252.12, 222.5
See application file for complete search history.

(56) References Cited

U.S. PATENT DOCUMENTS

| | | | |
|---|---|---|---|
| 3,845,770 A | 11/1974 | Theeuwes et al. | |
| 4,173,626 A | 11/1979 | Dempski et al. | |
| 4,326,525 A | 4/1982 | Swanson et al. | |
| 4,567,264 A | 1/1986 | Kluge et al. | |
| 4,902,514 A | 2/1990 | Barclay et al. | |
| 4,992,445 A | 2/1991 | Lawter et al. | |
| 5,001,139 A | 3/1991 | Lawter et al. | |
| 5,023,252 A | 6/1991 | Hseih | |
| 5,278,192 A | 1/1994 | Fung et al. | |
| 5,616,345 A | 4/1997 | Geoghegan et al. | |
| 6,303,607 B1 | 10/2001 | Wolff et al. | |
| 6,369,062 B1 | 4/2002 | Wolff et al. | |
| 6,423,705 B1 | 7/2002 | Tracey et al. | |
| 6,479,496 B1 | 11/2002 | Wolff | |
| 6,525,057 B2 | 2/2003 | Wolff | |
| 6,528,511 B2 | 3/2003 | Wolff | |
| 6,562,826 B1 | 5/2003 | Wolff | |
| 6,617,328 B2 | 9/2003 | Wolff et al. | |
| 6,620,814 B2 | 9/2003 | Wolff | |
| 6,677,342 B2 | 1/2004 | Wolff | |
| 6,706,689 B2 | 3/2004 | Coolidge et al. | |
| 6,864,258 B2 | 3/2005 | Wolff | |
| 6,930,111 B2 | 8/2005 | Ibrahim et al. | |
| 6,958,352 B2 | 10/2005 | Pei et al. | |
| 7,087,394 B2 | 8/2006 | Johnson et al. | |
| 2002/0042405 A1 | 4/2002 | Schuh | |
| 2002/0052377 A1 | 5/2002 | Wolff et al. | |
| 2003/0055027 A1 | 3/2003 | Schun | |
| 2003/0069221 A1 | 4/2003 | Kosoglou et al. | |
| 2003/0181352 A1 | 9/2003 | Ibrahim et al. | |
| 2003/0220310 A1 | 11/2003 | Schuh | |
| 2003/0220312 A1 | 11/2003 | Schuh | |
| 2004/0097514 A1 | 5/2004 | Wolff et al. | |
| 2004/0198693 A1 | 10/2004 | Deninno et al. | |
| 2005/0020682 A1 | 1/2005 | Newell et al. | |

(Continued)

FOREIGN PATENT DOCUMENTS

| | | |
|---|---|---|
| EP | 1541175 | 6/2005 |
| FR | 2805463 | 8/2001 |
| WO | WO 00/13687 | 3/2000 |
| WO | WO 02/07716 | 1/2002 |
| WO | WO 02/09761 | 2/2002 |

(Continued)

OTHER PUBLICATIONS

DeQuattro et al (Comparative Antianginal Efficacy and Tolerability of Ranolazine in Diabetic and Nondiabetic Patients: Results of the MARISA Trial, ABSTRACTS—Myocardial Ischemia and Infarction, pp. 338, JACC Feb. 2001).*

(Continued)

*Primary Examiner* — San-Ming Hui
*Assistant Examiner* — Kathrien Cruz
(74) *Attorney, Agent, or Firm* — Sheppard Mullin Richter & Hampton LLP

(57) ABSTRACT

Methods are provided for treating diabetes, lowering plasma level of HbA1c, glucose plasma levels, total cholesterol plasma level, and/or triglyceride plasma level while increasing HDL cholesterol levels and delaying onset of diabetic retinopathy in a diabetic, pre-diabetic, or non-diabetic mammal while minimizing undesirable side effects.

4 Claims, 6 Drawing Sheets

(56) References Cited

U.S. PATENT DOCUMENTS

| | | |
|---|---|---|
| 2005/0054695 A1 | 3/2005 | Ehring et al. |
| 2005/0059667 A1 | 3/2005 | Wolff |
| 2005/0153982 A1 | 7/2005 | Wolff |
| 2005/0245502 A1 | 11/2005 | Keller |
| 2006/0100189 A1 | 5/2006 | Gurtner et al. |
| 2006/0140953 A1 | 6/2006 | Newell et al. |
| 2006/0147521 A1 | 7/2006 | Wolff et al. |
| 2006/0172923 A1 | 8/2006 | Seipke et al. |
| 2006/0177502 A1 | 8/2006 | Sastry et al. |
| 2006/0205727 A1 | 9/2006 | Kaesemeyer |
| 2006/0217397 A1 | 9/2006 | Wolff et al. |
| 2008/0009503 A1 | 1/2008 | Wolff et al. |
| 2008/0153840 A1 | 6/2008 | Belardinelli et al. |
| 2008/0193530 A1 | 8/2008 | Blackburn et al. |
| 2008/0214555 A1 | 9/2008 | Jerling |
| 2008/0214556 A1 | 9/2008 | Jerling et al. |
| 2008/0233191 A1 | 9/2008 | Blackburn et al. |
| 2008/0248112 A1 | 10/2008 | Blackburn et al. |
| 2008/0299195 A1 | 12/2008 | Blackburn et al. |
| 2009/0111826 A1 | 4/2009 | Lange et al. |
| 2009/0203707 A1 | 8/2009 | Diamond et al. |
| 2009/0312340 A1 | 12/2009 | Wang et al. |
| 2010/0035890 A1 | 2/2010 | Lange et al. |
| 2010/0197701 A1 | 8/2010 | Wolff et al. |
| 2011/0183990 A1 | 7/2011 | Antzelevitch et al. |
| 2012/0004188 A1 | 1/2012 | Belardinelli et al. |

FOREIGN PATENT DOCUMENTS

| | | |
|---|---|---|
| WO | WO 03/008411 | 1/2003 |
| WO | WO 03/099281 | 12/2003 |
| WO | WO 2008/100992 | 8/2008 |
| WO | WO 2008/147417 | 12/2008 |
| WO | WO 2009/102886 | 8/2009 |

OTHER PUBLICATIONS

Stumvoli (Metabolic Effects of Metformin in Non-insulin-Dependent Diabetes Mellitus, The New England Journal of Medicine, Aug. 1995, pp. 550-554).*
U.S. Appl. No. 12/912,527, filed Oct. 20, 2010, Blackburn et al.
"Diabetes Control and Complications Trial, National Institute of Diabetes and Digestive and KidneyAW Diseases (NIDDK)," Results of the DCCT are reported in the New England Journal of Medicine, vol. 14, p. 329 (1993).
Abrams et al., "Ranolazine", *Nat Rev Drug Discov.*, 5(6):453-5 (2006).
Barnett et al., "The Longitudinal Effect of Inhibiting Fatty Acid Oxidation in Diabetic Rats Fed a HighFat Diet," Database Biosis Online! Biosciences Information Service, vol. 24, No. 8, pp. 360-362 (1992).
Chaitman et al., "Anti-ischemic effects and long-term survival during ranolazine monotherapy in patients with chronic severe angina" (2004) *J Am Coll Cardiol*, 43(8):1375-82 (2004).
Chaitman et al., "Effects of ranolazine with atenolol, amlodipine, or diltiazem on exercise tolerance and angina frequency in patients with severe chronic angina: a randomized controlled trial" *JAMA*, 291(3):309-16, (Nov. 2004).
Chaitman et al., "Efficacy of ranolazine as add-on therapy for chronic angina in elderly patients" *Circulation*, vol. 106 (19 Suppl. II): 330; Abstract No. 1649 (2002).
Chaitman et al., "Improved exercise capacity using a novel pFOX inhibitor as antianginal therapy: results of the combination assessment of ranolazine in stable angina (CARISA)", *Circulation: Late Breaking Clinical Trial Abstracts*, 104; pp. 1-2 (2001).
Chaitman et al., "Improved exercise performance on ranolazine in patients with chronic angina and a history of heart failure: The MARISA Trial", *J Am Coll Cardiol*, 37 (Suppl A):149A-150A; Abstract No. 1055-74 (2001).
Chaitman, "Measuring antianginal drug efficacy using exercise testing for chronic angina: improved exercise performance with ranolazine, a pFOX inhibitor", *Curr Probl Cardiol*, 27(12):527-55 (2002).
Chaitman, "Ranolazine for the treatment of chronic angina and potential use in other cardiovascular conditions", *Circulation*, 113:2462-2472 (2006).
Chaitman, "When should ranolazine be considered for the treatment of chronic angina?", *Nat Clin Pract Cardiovasc Med*, 3(11):590-1 (2006).
Chen et al., SNP 51103Y in the Cardiac Sodium Channel Gene SCN5A is Associated with Cardiac Arrhythmias and Sudden Death in a White Family, J Med Genet, 2002; 39: 913-915.
Chiang et al., "The long QT Syndromes: Genetic Basis and Clinical Implications," Journal of the American College of Cardiology, vol. 36, No. 1, pp. 1-12 (2000).
El-Sherif et al., "QTU Prolongation and Polymorphic Ventricular Tachyarrhythmias Due toBradycardia-Dependent Early Afterdepolarizations," Circulation Research, vol. 63, No. 2, pp. 286-305 (1988).
Glatter et al., "Chemical Cardioversion of Artrial Fibrillation or Flutter with Ibutilide in Patients Receiving Amiodarone Therapy," Circulation, vol. 103, pp. 253-257 (2001).
Grundy et al., "Prevention conference VI: Diabetes and Cardiovascular Disease Executive Summary Conference Proceeding Healthcare for Professionals from a Special Writing Group of the American Heart Associate," Circulation, vol. 105, pp. 2231-2239 (2002).
Grynberg, Modifications due Metabolisme Energetique Cardiaque Chez le Diabetique, Diabetes adn Metabolisms, vo. 27, No. 5, Nov. 2001, pp. 4S12-4S19, p. 4S16, col. 2, line 5, p. 4S17, col. 1, line 36.
Hanck et al., "Modification of Inactivation in Cardiac Sodium Channels: Ionic Current Studies with Anthopleurin-A Toxin," J. Gen. Physiol., vol. 106, pp. 601-616 (1995).
Morrow et al., "B-type natriuretic peptide and the effect of ranolazine in patients with non-ST elevation acute coronary syndromes in the MERLIN-TIMI 36 trial", *Circulation, Supplemental II* 116(16):382: Abstract 1788 (2007).
Morrow et al., "Effect of ranolizine on hemoglobin a1c in the MERLIN-TIMI 36 randomized controlled trial", *Circulation* 116(16):Supplemental 539-540: Abstract 2453 (2007).
Morrow et al., "Effects of ranolazine on recurrent cardiovascular events in patients with non-ST-elevation acute coronary syndromes—The MERLIN-TIMI 36 Randomized Trial", *JAMA* 297(16):1775-1783; including Web-Only content (2007).
Morrow et al., "Evaluation of a novel anti-ischemic agent in acute coronary syndromes: design and rationale for the metabolic efficiency with ranolazine for less ischemia in non-ST-elevation acute coronary syndromes (MERLIN)-TIMI 36 trial", *Am Heart J* 151(6):1186.e1-1186.e9 (2006).
Moss et al., Ranolazine Shortens Repolarization in Patients with Sustained Inward Sodium Current Due to Type-3 Long QT Syndrome, J Cardiovasc Electrophysiol, 2008; 19(12): 1289-1293.
Office Action for U.S. Appl. No. 11/756,499, dated Apr. 1, 2010.
Office Action for U.S. Appl. No. 11/756,499, dated May 4, 2012.
Office Action for U.S. Appl. No. 11/756,499, dated Oct. 3, 2011.
Office Action for U.S. Appl. No. 11/756,499, dated Sep. 22, 2009.
Office Action for U.S. Appl. No. 12/553,841, dated Feb. 1, 2012.
Office Action for U.S. Appl. No. 12/556,417, dated Dec. 20, 2011.
Office Action for U.S. Appl. No. 12/556,417, dated Mar. 21, 2011.
Office Action for U.S. Appl. No. 12/755,931, dated Apr. 27, 2011.
Office Action for U.S. Appl. No. 12/755,931, dated Feb. 28, 2012.
Office Action for U.S. Appl. No. 12/755,931, dated Sep. 12, 2011.
Office Action for U.S. Appl. No. 12/779,753, dated Dec. 19, 2012.
Office Action for U.S. Appl. No. 12/779,753, dated Dec. 21, 2011.
Office Action for U.S. Appl. No. 12/779,753, dated Jun. 16, 2011.
Office Action for U.S. Appl. No. 12/972,949, dated Oct. 26, 2012.
Press release of (Feb. 7, 2007) "MERLIN TIMI-36 study accepted as late breaking clinical trial at American College of Cardiology Annual Scientific Session" [retrieved on Feb. 7, 2007] Retrieved from the Internet: URL: http://prnewswire.com.
Press release of (Feb. 9, 2006) "CV Therapeutics announces MERLIN TIMI-36 study to continue as planned based on interim analysis" [retrieved on Feb. 7, 2007] Retrieved from the Internet: URL: http://prnewswire.com.

(56) References Cited

OTHER PUBLICATIONS

Press release of (Mar. 6, 2007) "CV Therapeutics Announces Topline MERLIN TIMI-36 Results" [retrieved on Oct. 3, 2008] Retrieved from the Internet: URL: http://prnewswire.com.

Press release of (May 25, 2006) "CV Therapeutics announces completion of MERLIN TIMI-36 enrollment" [retrieved on Feb. 7, 2007] Retrieved from the Internet: URL: http://prnewswire.com.

Press release of (Jun. 21, 2006) "MERLIN TIMI-36 study design published in American Heart Journal" [retrieved on Feb. 7, 2007] Retrieved from the Internet: URL: http://prnewswire.com.

Press release of (Jul. 7, 2006) "CV Therapeutics announces MERLIN TIMI-36 Study to continue as planned based on final scheduled DSMB meeting" [retrieved on Feb. 7, 2007] Retrieved from the Internet: URL: http//prnewswire.com.

Press release of (Jul. 29, 2004) "CV Therapeutics and FDA agree to special protocol assessment for outcomes study to support potential use of Ranexa™ as first-line therapy for chronic angina" [retrieved on Feb. 7, 2007] Retrieved from the Internet: URL: http://prnewswire.com.

Press release of (Sep. 26, 2007) "CV Therapeutics completes MERLIN-TIMI-36 Study" [retrieved on Feb. 7, 2007] Retrieved from the Internet: URL: http://prnewswire.com.

Press release of (Oct. 11, 2004) "CV Therapeutics initiates MERLIN TIMI-36 Study of Ranexa™" [retrieved on Feb. 7, 2007] Retrieved from the Internet: URL: http://prnewswire.com.

Press release of Mar. 19, 2011 "CV Therapeutics Announces Phase III Marisa Analysis Suggesting Potential Benefit in Diabetic Patients with Chronic Angina" [retrieved Apr. 30, 2012], retrieved from the Internet: URL: www.evaluatepharma.com.

Randle, "Apparent Reversal of Insulin Resistance in Cardiac Muscle in Alloxan Diabetes by 2 BromoStearate," Nature, vol. 221, No. 5182, p. 777 (1969).

Redberg et al., "Prevention Conference VI: Diabetes and Cardiovascular Disease, Writing Group III: Risk Assessment in Persons with Diabetes," Circulation, vol. 105, pp. e144-e152 (2002).

Rohlfing et al., "Defining the relationship between plasma glucose and HbA1c," Diabetes Care, vol. 25, No. 2, pp. 275-278 (2002).

Sabbah, et al., Partial fatty acid oxidation inhibitors—a potentially new class of drugs for heart failure, Euro J Heart Failure, 4:3-6 (2002).

Scirica et al., "Baseline clinical risk and recurrent ischemia as detected on continuous ECG (CECG) monitoring in patients with non-ST-elevation acute coronary syndrome in the MERLIN-TIMI 36 trial", *American Heart Association*, 116:II_722; Abstract No. 3211 (2007).

Scirica et al., "Clinical outcomes in patients with diabetes or the metabolic syndrome with non-ST-elevation acute coronary syndrome in the MERLIN-TIMI 36 trial", *Circulation*, pp. 64-65; Abstract No. P535 (2007).

Splawski et al., Variant of SCN5A Sodium Channel Implicated in Risk of Cardiac Arrhythmia, Science Magazine, vol. 297, 3, pp. 1333-1336 (2003).

Stanley et al., "Regulation of Myocardial Carbohydrate Metabolism Under Normal and Ischaemic Conditions," Cardiovascular Research, vol. 33, No. 2, pp. 243-257 (1997).

Uusitupa et al., "Ten-year cardiovascular mortality in relation to risk factors and abnormalities in lipoprotein composition in type 2 [non-insulin-dependent] diabetic and non-diabetic subjects", *Diabetologia* vol. 36, pp. 1175-1184 (1993).

Van Norstrand et al., Over Representation of the Pro-Arrhythmic, Sudden Death Predisposing Sodium Channel Polymorphism, S1103Y, in a Population Based Cohort of African American Sudden Infant Death Syndrome, Heart Rhythm, 2008; 5(5): 712-715.

Viswanathan et al., "Pause Induced Early Afterdepolarizations in the long QT Syndrome: A Simulation Study," Cardiovascular Research, vol. 42, pp. 530-542 (1999).

Wedekind et al., De Novo Mutation in the SCN5A Gene Associated with Early Onset of Sudden Infant Death, Circulation, 2001; 104: 1158-1164.

Wolff et al., "MARISA: Monotherapy assessment of ranolazine in stable angina", *JACC*, p. 408A Abstract No. 1196-101 (2000).

\* cited by examiner

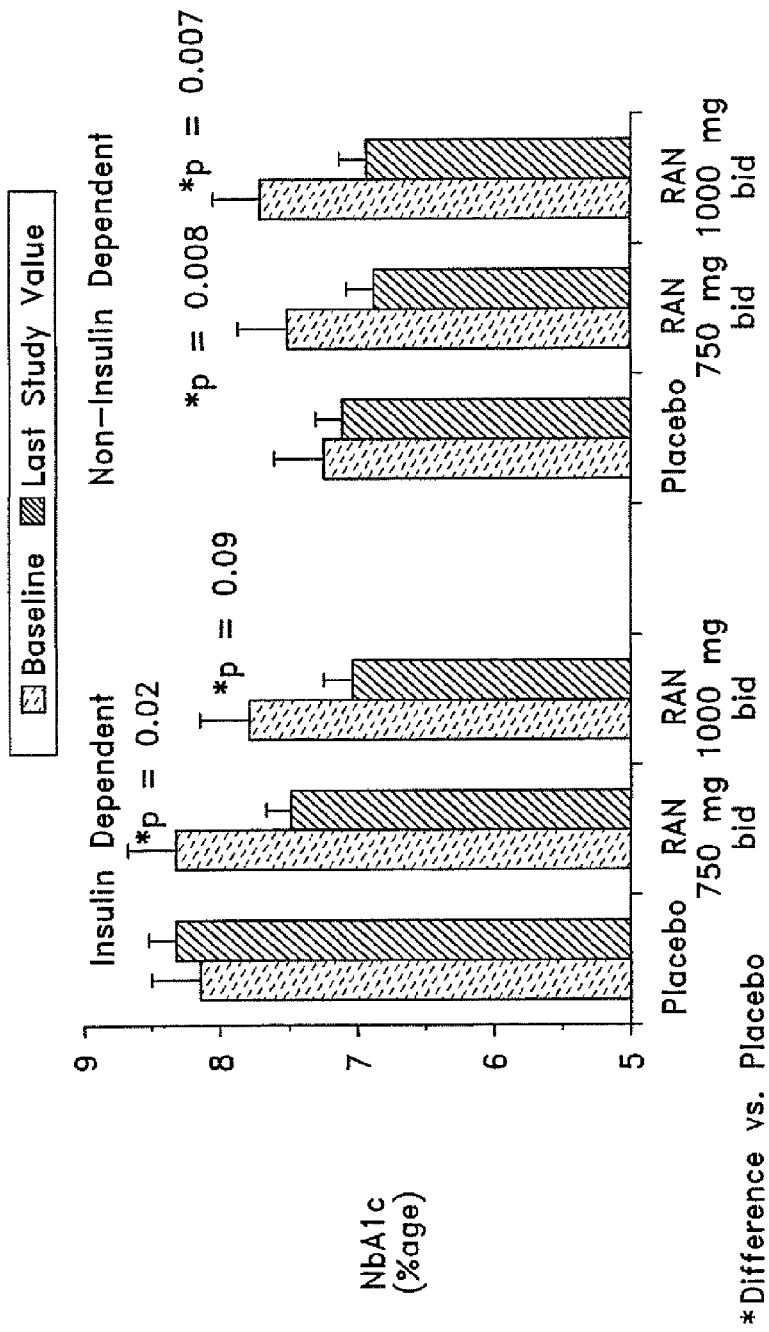

METHOD OF TREATING DIABETES

CROSS-REFERENCE TO RELATED APPLICATIONS

This is a continuation of U.S. application Ser. No. 12/755,931, filed Apr. 7, 2010, now U.S. Pat. No. 8,314,104, which application is a continuation of U.S. application Ser. No. 10/443,314, filed May 21, 2003, now abandoned, which claims priority to U.S. Provisional Application Ser. No. 60/382,781, filed May 21, 2002, and to U.S. Provisional Application Ser. No. 60/459,332, filed Mar. 31, 2003, the complete disclosures of which are hereby incorporated by reference.

FIELD OF THE INVENTION

Methods are provided for treating diabetes, lowering plasma level of HbA1c, glucose plasma levels, total cholesterol plasma levels, and/or triglyceride plasma level while increasing HDL cholesterol levels and delaying onset of diabetic retinopathy in a diabetic, pre-diabetic, or non-diabetic mammal while minimizing undesirable side effects.

BACKGROUND

Diabetes mellitus is a disease characterized by hyperglycemia; altered metabolism of lipids, carbohydrates and proteins; and an increased risk of complications from vascular disease. Diabetes is an increasing public health problem, as it is associated with both increasing age and obesity.

There are two major types of diabetes mellitus: 1) Type I, also known as insulin dependent diabetes (IDDM) and 2) Type II, also known as insulin independent or non-insulin dependent diabetes (NIDDM). Both types of diabetes mellitus are due to insufficient amounts of circulating insulin and a decrease in the response of peripheral tissue to insulin.

Type I diabetes results from the body's failure to produce insulin, the hormone that "unlocks" the cells of the body, allowing glucose to enter and fuel them. The complications of Type I diabetes include heart disease and stroke; retinopathy (eye disease); kidney disease (nephropathy); neuropathy (nerve damage); as well as maintenance of good skin, foot and oral health.

Type II diabetes results from the body's inability to either produce enough insulin or the cells inability to use the insulin that is naturally produced by the body. The condition where the body is not able to optimally use insulin is called insulin resistance. Type II diabetes is often accompanied by high blood pressure and this may contribute to heart disease. In patients with type II diabetes mellitus, stress, infection, and medications (such as corticosteroids) can also lead to severely elevated blood sugar levels. Accompanied by dehydration, severe blood sugar elevation in patients with type II diabetes can lead to an increase in blood osmolality (hyperosmolar state). This condition can lead to coma.

Insulin lowers the concentration of glucose in the blood by stimulating the uptake and metabolism of glucose by muscle and adipose tissue. Insulin stimulates the storage of glucose in the liver as glycogen, and in adipose tissue as triglycerides. Insulin also promotes the utilization of glucose in muscle for energy. Thus, insufficient insulin levels in the blood, or decreased sensitivity to insulin, gives rise to excessively high levels of glucose and triglycerides in the blood.

The early symptoms of untreated diabetes mellitus are related to elevated blood sugar levels, and loss of glucose in the urine. High amounts of glucose in the urine can cause increased urine output and lead to dehydration. Dehydration causes increased thirst and water consumption. The inability to utilize glucose energy eventually leads to weight loss despite an increase in appetite. Some untreated diabetes patients also complain of fatigue, nausea, and vomiting. Patients with diabetes are prone to developing infections of the bladder, skin, and vaginal areas. Fluctuations in blood glucose levels can lead to blurred vision. Extremely elevated glucose levels can lead to lethargy and coma (diabetic coma).

People with glucose levels between normal and diabetic have impaired glucose tolerance (IGT). This condition is also called pre-diabetes or insulin resistance syndrome. People with IGT do not have diabetes, but rather have blood glucose levels that are higher than normal but not yet high enough to be diagnosed as diabetes. Their bodies make more and more insulin, but because the tissues don't respond to it, their bodies can't use sugar properly. Recent studies have shown that IGT itself may be a risk factor for the development of heart disease. It is estimated that people with pre-diabetes have a 1.5-fold risk of cardiovascular disease compared to people with normal blood glucose. People with diabetes have a 2- to 4-fold increased risk of cardiovascular disease.

High blood levels of glucose and triglycerides cause the thickening of capillary basement membrane, which results in the progressive narrowing of vessel lumina. The vasculopathies give rise to conditions such as diabetic retinopathy, which may result in blindness, coronary heart disease, intercapillary glomerulosclerois, neuropathy, and ulceration and gangrene of the extremities.

The toxic effects of excess plasma levels of glucose include the glycosylation of cells and tissues. Glycosylated products accumulate in tissues and may eventually form cross-linked proteins, which cross-linked proteins are termed advanced glycosylation end products. It is possible that non-enzymatic glycosylation is directly responsible for expansion of the vascular matrix and vascular complications of diabetes. For example, glycosylation of collagen results in excessive cross-linking, resulting in atherosclerotic vessels. Also, the uptake of glycosylated proteins by macrophages stimulates the secretion of pro-inflammatory cytokines by these cells. The cytokines activate or induce degradative and proliferative cascades in mesenchymal and endothelial cells respectively.

The glycosylation of hemoglobin provides a convenient method to determine an integrated index of the glycemic state. The level of glycosylated proteins reflects the level of glucose over a period of time and is the basis of an assay referred to as the hemoglobulin A1 (HbA1c) assay HbA1c reflects a weighted average of blood glucose levels during the previous 120 days; plasma glucose in the previous 30 days contributes about 50% to the final result in an HbA1c assay. The test for A1c (also known as HbA1c, glycohemoglobin, or glycated hemoglobin) indicates how well diabetes has been controlled over the last few months. The closer A1c is to 6%, the better the control of diabetes. For every 30 mg/dl increase in A1c blood glucose, there is a 1% increase in A1c, and the risk of complications increases.

Another explanation for the toxic effects of hyperglycemia includes sorbitol formation. Intracellular glucose is reduced to its corresponding sugar alcohol, sorbitol, by the enzyme aldose reductase; the rate of production of sorbitol is determined by the ambient glucose concentration. Thus, tissues such as lens, retina, arterial wall and schwann cells of peripheral nerves have high concentrations of sorbitol.

Hyperglycemia also impairs the function of neural tissues because glucose competes with myoinositol resulting in reduction of cellular concentrations and, consequently, altered nerve function and neuropathy.

Increased triglyceride levels are also a consequence of insulin deficiency. High triglyceride levels are also associated with vascular disease.

Thus, controlling blood glucose and triglyceride levels is a desirable therapeutic goal. A number of oral antihyperglycemic agents are known. Medications that increase the insulin output by the pancreas include sulfonylureas (including chlorpropamide [Orinase®], tolbutamide [Tolinase®], glyburide [Micronase®], glipizide [Glucotrol®], and glimepiride [Amaryl®]) and meglitinides (including reparglinide [Prandin®] and nateglinide [Starlix®]). Medications that decrease the amount of glucose produced by the liver include biguanides (including metformin [Glucophage®]. Medications that increase the sensitivity of cells to insulin include thazolidinediones (including troglitazone [Resulin®], pioglitazone [Actose] and rosiglitazone [Avandia®]). Medications that decrease the absorption of carbohydrates from the intestine include alpha glucosidase inhibitors (including acarbose [Precose®] and miglitol [Glyset®]). Actos® and Avandia® can change the cholesterol patterns in diabetics. HDL (or good cholesterol) increases on these medications. Precose® works on the intestine; its effects are additive to diabetic medications that work at other sites, such as sulfonylureas. ACE inhibitors can be used to control high blood pressure, treat heart failure, and prevent kidney damage in people with hypertension or diabetes. ACE inhibitors or combination products of an ACE inhibitor and a diuretic, such as hydrochlorothazide, are marketed. However, none of these treatments is ideal.

Blood pressure control can reduce cardiovascular disease (for example, myocardial infarction and stroke) by approximately 33% to 50% and can reduce microvascular disease (eye, kidney, and nerve disease) by approximately 33%. The Center for Disease Control has found that for every 10 millimeters of mercury (mm Hg) reduction in systolic blood pressure, the risk for any complication related to diabetes is reduced by 12%. Improved control of cholesterol and lipids (for example HDL, LDL, and triglycerides) can reduce cardiovascular complications by 20% to 50%.

Total cholesterol should be less than 200 mg/dl. Target levels for high density lipoprotein (HDL or "good" cholesterol) are above 45 mg/dl for men and above 55 mg/dl for women, while low density lipoprotein (LDL or "bad" cholesterol) should be kept below 100 mg/dl. Target triglyceride levels for women and men are less than 150 mg/dl.

Approximately 50% of patients with diabetes develop some degree of diabetic retinopathy after 10 years of diabetes, and 80% of diabetics have retinopathy after 15 years.

In a study (the DCCT study) conducted by the National Institute of Diabetes and Disgestive and Kidney Diseases (NIDDK) it was shown that keeping blood glucose levels as close to normal as possible slows the onset and progression of eye, kidney, and nerve diseases caused by diabetes.

In the Diabetes Prevention Program (DPP) clinical trial type 2 diabetics were studied. The DPP study found that over the 3 years of the study, diet and exercise sharply reduced the chances that a person with IGT would develop diabetes. Administration of metformin (Glucophage®) also reduced risk, although less dramatically.

The DCCT study showed a correlation between HbA1c and the mean blood glucose. The DPP study showed that HbA1c is strongly correlated with adverse outcome risk.

In a series of reports from the American Heart Association's Prevention Conference VI: Diabetes and Cardiovascular Disease it was reported that about two-thirds of people with diabetes eventually die of heart or blood vessel disease. Studies also showed that the increase in cardiovascular disease risk associated with diabetes can be lessened by controlling individual risk factors such as obesity, high cholesterol, and high blood pressure.

It is important for a person suffering from diabetes to reduce the risk of complications such as cardiovascular disease, retinopathy, nephropathy, and neuropathy. It is also important for diabetics to reduce total cholesterol and triglyceride levels to reduce cardiovascular complications. Reduction of these possible complication risks is also important for a person suffering from IGT (a pre-diabetic).

Thus, if HbA1c and blood glucose levels can be controlled, the risk of complications such as cardiovascular disease, retinopathy, nephropathy, and neuropathy can be reduced or their onset delayed. If total cholesterol and triglyceride levels can be reduced, then cardiovascular complications can be reduced.

U.S. Pat. No. 4,567,264, the specification of which is incorporated herein by reference, discloses compounds that have been shown to be partial fatty acid oxidation inhibitors. One compound disclosed therein, (±)-N-(2,6-dimethylphenyl)-4-[2-hydroxy-3-(2-methoxyphenoxy)-propyl]-1-piperazineacetamide (known as ranolazine) is undergoing clinical trials for the treatment of angina. Ranolazine has also been found to be useful for the treatment of congestive heart failure and arrhythmia. During angina clinical trials using ranolazine, it was surprisingly discovered that treatment of diabetic angina patients with ranolazine was not only effective in treating angina, but also reduced hemoglobulin A1 (HbA1c) levels and, over the long term, reduced triglyceride levels. Ranolazine was also found to reduce triglyceride levels in non-diabetic patients. Ranolazine was also found to lower glucose plasma levels and, over the long term, total cholesterol levels, while increasing HDL cholesterol levels. Thus, ranolazine provides a method of treating diabetes pre-diabetes, or the non-diabetes condition by reducing the levels of potentially toxic metabolites in blood and/or complications associated with diabetes. Ranolazine also can reduce the number of medications necessary for a patient with both cardiovascular problems and diabetes or pre-diabetes.

SUMMARY OF THE INVENTION

It is an object of this invention to provide an effective method of treating diabetes, in a mammal while minimizing undesirable side effects. Accordingly, in a first aspect, the invention relates to a method of treating diabetes mellitus in a mammal, comprising administration of a therapeutically effective amount of a partial fatty acid oxidation (pfox) inhibitor to a mammal in need thereof.

In a second aspect, the invention relates to a method of treating diabetes in a mammal comprising administration of a therapeutically effective amount of a partial fatty acid oxidation inhibitor of Formula I:

Formula I

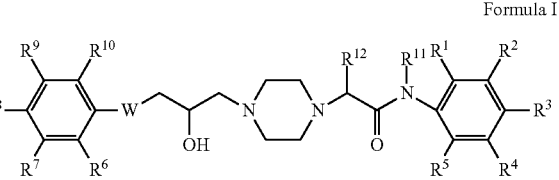

wherein:

$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, or N-optionally substituted alkylamido, provided that when. $R^1$ is methyl, $R^4$ is not methyl;

or $R^2$ and $R^3$ together form —OCH$_2$O—;

$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, or di-lower alkyl amino; or $R^6$ and $R^7$ together form —CH═CH—CH═CH—; or $R^7$ and $R^8$ together form —O—CH$_2$O—;

$R^{11}$ and $R^{12}$ are each independently hydrogen or lower alkyl; and

W is oxygen or sulfur;

or a pharmaceutically acceptable salt or ester thereof, or an isomer thereof.

The compounds of Formula I are disclosed in more detail in U.S. Pat. No. 4,567,264, the complete disclosure of which is hereby incorporated by reference. A preferred compound of this invention is ranolazine, which is named N-(2,6-dimethylphenyl)-4-[2-hydroxy-3-(2-methoxyphenoxy)propyl]-1-piperazineacetamide, as a racemic mixture, or an isomer thereof, or a pharmaceutically acceptable salt thereof.

A third aspect of this invention is a method of treating diabetes mellitus in a mammal comprising administering a therapeutically effective amount of ranolazine.

A fourth aspect In a sixth aspect, the invention relates to a method of treating diabetes mellitus in a mammal comprising administration of a therapeutically effective amount of a partial fatty acid oxidation inhibitor of Formula II:

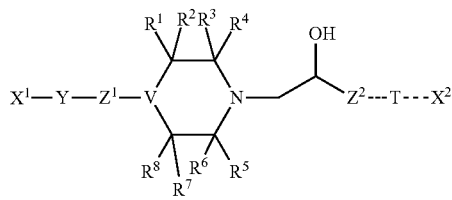

Formula II wherein:

$R^1$, $R^2$, $R^3$, $R^4$, $R^5$, $R^6$, $R^7$, and $R^8$ are hydrogen, lower alkyl, or —C(O)R;

in which R is —OR$^9$ or —NR$^9$R$^{10}$, where $R^9$ and $R^{10}$ are hydrogen or lower alkyl; or $R^1$ and $R^2$, $R^3$ and $R^4$, $R^5$ and $R^6$, $R^7$ and $R^8$, when taken together with the carbon to which they are attached, represent carbonyl; or $R^1$ and $R^5$, or $R^1$ and $R^7$, or $R^3$ and $R^5$, or $R^3$ and $R^7$, when taken together form a bridging group —(CR$^{12}$R$^{13}$)$_n$—, in which n is 1, 2 or 3, and $R^{12}$ and $R^{13}$ are independently hydrogen or lower alkyl; with the proviso that the maximum number of carbonyl groups is 2; the maximum number of —C(O)NR$^9$R$^{10}$ groups is 1; and the maximum number of bridging groups is 1;

T is oxygen, sulfur, or NR$^{11}$, in which $R^{11}$ is hydrogen or lower alkyl;

V is —N<, —CH<, or —N—CH<;

$X^1$ is hydrogen, optionally substituted lower alkyl, optionally substituted cycloalkyl, optionally substituted aryl, or optionally substituted heteroaryl;

$X^2$ is optionally substituted aryl or optionally substituted heteroaryl;

Y is optionally substituted monocyclic heteroaryl; and $Z^1$ and $Z^2$ are independently optionally substituted alkylene of 1-4 carbon atoms.

The compounds of Formula II are disclosed in more detail in U.S. Provisional Patent Application Ser. No. 60/306,621 (now U.S. patent application Ser. No. 10/198,237), the complete disclosures of which are hereby incorporated by reference.

A fifth aspect of this invention is a method of treating diabetes mellitus comprising administering a therapeutically effective amount of a partial fatty acid oxidation inhibitor, namely 1-{4-[5-(4-trifluoromethylphenyl))-[1,2,4]-oxadiazol-3-ylmethyl]-piperazin-1-yl}-3-(2-methylbenzothiazol-1,5-yloxy)-propan-2-ol; as a racemic mixture, or an isomer thereof.

A sixth aspect of this invention is a method of lowering plasma level of HbA1c in a mammal, wherein the mammal is diabetic, non-diabetic, or pre-diabetic, comprising administration of a therapeutically effective amount of a partial fatty acid oxidation inhibitor to a mammal in need thereof.

A seventh aspect of this invention is a method of lowering plasma level of HbA1c in a mammal comprising administration of a therapeutically effective amount of a partial fatty acid oxidation inhibitor, wherein the partial fatty acid oxidation inhibitor is a compound Formula I:

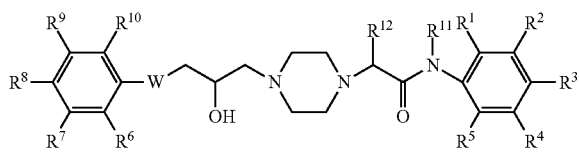

Formula I wherein:

$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, or N-optionally substituted alkylamido, provided that when $R^1$ is methyl, $R^4$ is not methyl;

or $R^2$ and $R^3$ together form —OCH$_2$O—;

$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, or di-lower alkyl amino; or $R^6$ and $R^7$ together form —CH═CH—CH═CH—; or $R^7$ and $R^8$ together form —O—CH$_2$O—;

$R^{11}$ and $R^{12}$ are each independently hydrogen or lower alkyl; and

W is oxygen or sulfur;

or a pharmaceutically acceptable salt or ester thereof, or an isomer thereof.

An eighth aspect of this invention is a method of lowering plasma HbA1c in a mammal, comprising administration of a therapeutically effective amount of a partial fatty acid oxidation inhibitor, wherein the partial fatty acid oxidation inhibitor is ranolazine, which is named. N-(2,6-dimethylphenyl)-4-[2-hydroxy-3-(2-methoxyphenoxy)propyl]-1-piperazineacetamide, as a racemic mixture, or an isomer thereof, or a pharmaceutically acceptable salt thereof.

A ninth aspect of this invention is a method of lowering plasma HbA1c in a mammal, comprising administration of a therapeutically effective amount of a partial fatty acid oxidation inhibitor, wherein the partial fatty acid oxidation inhibitor is a compound of Formula II:

Formula II

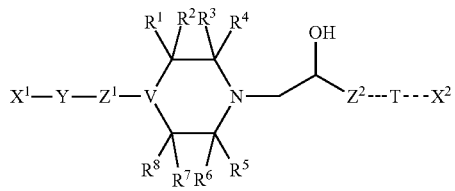

wherein:

$R^1$, $R^2$, $R^3$, $R^4$, $R^5$, $R^6$, $R^7$, and $R^8$ are hydrogen, lower alkyl, or —C(O)R;

in which R is —$OR^9$ or —$NR^9R^{10}$, where $R^9$ and $R^{10}$ are hydrogen or lower alkyl; or $R^1$ and $R^2$, $R^3$ and $R^4$, $R^5$ and $R^6$, $R^7$ and $R^8$, when taken together with the carbon to which they are attached, represent carbonyl; or $R^1$ and $R^5$, or $R^1$ and $R^7$, or $R^3$ and $R^5$, or $R^3$ and $R^7$, when taken together form a bridging group —$(CR^{12}R^{13})_n$—, in which n is 1, 2 or 3, and $R^{12}$ and $R^{13}$ are independently hydrogen or lower alkyl; with the proviso that the maximum number of carbonyl groups is 2; the maximum number of —$C(O)NR^9R^{10}$ groups is 1; and the maximum number of bridging groups is 1;

T is oxygen, sulfur, or $NR^{11}$, in which $R^{11}$ is hydrogen or lower alkyl;

V is —N<, —CH<, or —N—CH<;

$X^1$ is hydrogen, optionally substituted lower alkyl, optionally substituted cycloalkyl, optionally substituted aryl, or optionally substituted heteroaryl;

$X^2$ is optionally substituted aryl or optionally substituted heteroaryl;

Y is optionally substituted monocyclic heteroaryl; and $Z^1$ and $Z^2$ are independently optionally substituted alkylene of 1-4 carbon atoms.

A tenth aspect of this invention is a method of lowering plasma level of HbA1c in a mammal, comprising administration of a therapeutically effective amount of a partial fatty acid oxidation inhibitor, wherein the partial fatty acid oxidation inhibitor of Formula II is 1-{4-[5-(4-trifluoromethylphenyl))-[1,2,4]-oxadiazol-3-ylmethy]-piperazin-1-yl}-3-(2-methylbenzothiazol-1,5-yloxy)-propan-2-ol; as a racemic mixture, or an isomer thereof.

An eleventh aspect of this invention is a method of lowering triglyceride plasma level in a mammal, wherein the mammal is diabetic, non-diabetic, or pre-diabetic, comprising administration of a therapeutically effective amount of a partial fatty acid oxidation inhibitor to a mammal in need thereof.

A twelfth aspect of this invention is a method of lowering triglyceride plasma level in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor is a compound Formula I:

Formula I

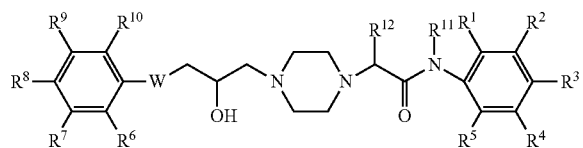

wherein:

$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, or N-optionally substituted alkylamido, provided that when $R^1$ is methyl, $R^4$ is not methyl;

or $R^2$ and $R^3$ together form —$OCH_2O$—;

$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, or di-lower alkyl amino; or $R^6$ and $R^7$ together form —CH=CH—CH=CH—; or $R^7$ and $R^8$ together form —O—$CH_2$O—;

$R^{11}$ and $R^{12}$ are each independently hydrogen or lower alkyl; and

W is oxygen or sulfur;

or a pharmaceutically acceptable salt or ester thereof, or an isomer thereof.

A thirteenth aspect of this invention is a method of lowering triglyceride plasma level in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor is ranolazine, which is named N-(2,6-dimethylphenyl)-4-[2-hydroxy-3-(2-methoxyphenoxy)propyl]-1-piperazineacetamide, as a racemic mixture, or an isomer thereof, or a pharmaceutically acceptable salt thereof.

A fourteenth aspect of this invention is a method of lowering triglyceride plasma level in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor is a compound of Formula II:

Formula II

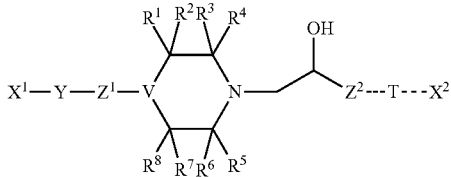

wherein:

$R^1$, $R^2$, $R^3$, $R^4$, $R^5$, $R^6$, $R^7$, and $R^8$ are hydrogen, lower alkyl, or —C(O)R;

in which R is —$OR^9$ or —$NR^9R^{10}$, where $R^9$ and $R^{10}$ are hydrogen or lower alkyl; or $R^1$ and $R^2$, $R^3$ and $R^4$, $R^5$ and $R^6$, $R^7$ and $R^8$, when taken together with the carbon to which they are attached, represent carbonyl; or $R^1$ and $R^5$, or $R^1$ and $R^7$, or $R^3$ and $R^5$, or $R^3$ and $R^7$, when taken together form a bridging group —$(CR^{12}R^{13})_n$—, in which n is 1, 2 or 3, and $R^{12}$ and $R^{13}$ are independently hydrogen or lower alkyl; with the proviso that the maximum number of carbonyl groups is 2; the maximum number of —$C(O)NR^9R^{10}$ groups is 1; and the maximum number of bridging groups is 1;

T is oxygen, sulfur, or $NR^{11}$, in which $R^{11}$ is hydrogen or lower alkyl;

V is —N<, —CH<, or —N—CH<;

$X^1$ is hydrogen, optionally substituted lower alkyl, optionally substituted cycloalkyl, optionally substituted aryl, or optionally substituted heteroaryl;

$X^2$ is optionally substituted aryl or optionally substituted heteroaryl;

Y is optionally substituted monocyclic heteroaryl; and $Z^1$ and $Z^2$ are independently optionally substituted alkylene of 1-4 carbon atoms.

A fifteenth aspect of this invention is a method of lowering triglyceride plasma level in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor of Formula II is 1-{4-[5-(4-trifluoromethylphenyl))-[1,2,4]-oxadiazol-3-yl-methyl]-piperazin-1-yl}-3-(2-methylbenzothiazol-1,5-yloxy)-propan-2-ol; as a racemic mixture, or an isomer thereof.

A sixteenth aspect of this invention is a method of lowering glucose plasma level in a mammal, wherein the mammal is diabetic, non-diabetic, or pre-diabetic, comprising administration of a therapeutically effective amount of a partial fatty acid oxidation inhibitor to a mammal in need thereof.

A seventeenth aspect of this invention is a method of lowering glucose plasma level in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor is a compound Formula I:

Formula I wherein:
$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, or N-optionally substituted alkylamido, provided that when $R^1$ is methyl, $R^4$ is not methyl;
or $R^2$ and $R^3$ together form —OCH$_2$O—;
$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, or di-lower alkyl amino; or
$R^6$ and $R^7$ together form —CH=CH—CH=CH—; or
$R^7$ and $R^8$ together form —O—CH$_2$O—;
$R^{11}$ and $R^{12}$ are each independently hydrogen or lower alkyl; and
W is oxygen or sulfur;
or a pharmaceutically acceptable salt or ester thereof, or an isomer thereof.

An eighteenth aspect of this invention is a method of lowering glucose plasma level in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor is ranolazine, which is named N-(2,6-dimethylphenyl)-4-[2-hydroxy-3-(2-methoxyphenoxy)propyl]-1-piperazineacetamide, as a racemic mixture, or an isomer thereof, or a pharmaceutically acceptable salt thereof.

A nineteenth aspect of this invention is a method of lowering glucose plasma level in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor is a compound of Formula II:

Formula II wherein:
$R^1$, $R^2$, $R^3$, $R^4$, $R^5$, $R^6$, $R^7$, and $R^8$ are hydrogen, lower alkyl, or —C(O)R;
in which R is —OR$^9$ or —NR$^9$R$^{10}$, where $R^9$ and $R^{10}$ are hydrogen or lower alkyl; or
$R^1$ and $R^2$, $R^3$ and $R^4$, $R^5$ and $R^6$, $R^7$ and $R^8$, when taken together with the carbon to which they are attached, represent carbonyl; or
$R^1$ and $R^5$, or $R^1$ and $R^7$, or $R^3$ and $R^5$, or $R^3$ and $R^7$, when taken together form a bridging group —(CR$^{12}$R$^{13}$)$_n$—, in which n is 1, 2 or 3, and $R^{12}$ and $R^{13}$ are independently hydrogen or lower alkyl; with the proviso that the maximum number of carbonyl groups is 2; the maximum number of —C(O)NR$^9$R$^{10}$ groups is 1; and the maximum number of bridging groups is 1;
T is oxygen, sulfur, or NR$^{11}$, in which $R^{11}$ is hydrogen or lower alkyl;
V is —N<, —CH<, or —N—CH<;
$X^1$ is hydrogen, optionally substituted lower alkyl, optionally substituted cycloalkyl, optionally substituted aryl, or optionally substituted heteroaryl;
$X^2$ is optionally substituted aryl or optionally substituted heteroaryl;
Y is optionally substituted monocyclic heteroaryl; and
$Z^1$ and $Z^2$ are independently optionally substituted alkylene of 1-4 carbon atoms.

A twentieth aspect of this invention is a method of lowering glucose plasma level in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor of Formula II is 1-{4-[5-(4-trifluoromethylphenyl))-[1,2,4]-oxadiazol-3-yl-methyl]-piperazin-1-yl}-3-(2-methylbenzothiazol-1,5-yloxy)-propan-2-ol; as a racemic mixture, or an isomer thereof.

A twenty-first aspect of this invention is a method of lowering total cholesterol plasma level in a mammal, wherein the mammal is diabetic, non-diabetic, or pre-diabetic, comprising administration of a therapeutically effective amount of a partial fatty acid oxidation inhibitor to a mammal in need thereof.

A twenty-second aspect of this invention is a method of lowering total cholesterol plasma level in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor is a compound Formula I:

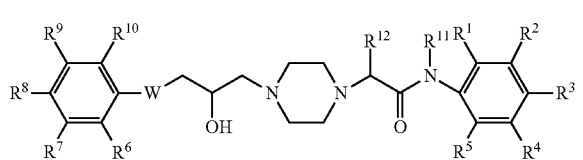

Formula I wherein:

$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, or N-optionally substituted alkylamido, provided that when $R^1$ is methyl, $R^4$ is not methyl;

or $R^2$ and $R^3$ together form —$OCH_2O$—;

$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, or di-lower alkyl amino; or $R^6$ and $R^7$ together form —CH=CH—CH=CH—; or $R^7$ and $R^8$ together form —O—$CH_2O$—;

$R^{11}$ and $R^{12}$ are each independently hydrogen or lower alkyl; and

W is oxygen or sulfur;

or a pharmaceutically acceptable salt or ester thereof, or an isomer thereof.

A twenty-third aspect of this invention is a method of lowering total cholesterol plasma level in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor is ranolazine, which is named N-(2,6-dimethylphenyl)-4-[2-hydroxy-3-(2-methoxyphenoxy)propyl]-1-piperazineacetamide, as a racemic mixture, or an isomer thereof, or a pharmaceutically acceptable salt thereof.

A twenty-fourth aspect of this invention is a method of lowering total cholesterol plasma level in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor is a compound of Formula II:

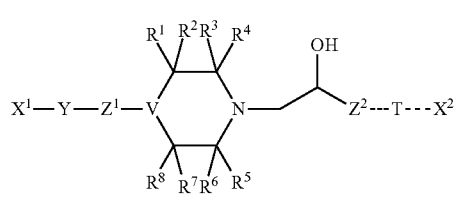

Formula II wherein:

$R^1$, $R^2$, $R^3$, $R^4$, $R^5$, $R^6$, $R^7$, and $R^8$ are hydrogen, lower alkyl, or —C(O)R;

in which R is —$OR^9$ or —$NR^9R^{10}$, where $R^9$ and $R^{10}$ are hydrogen or lower alkyl; or $R^1$ and $R^2$, $R^3$ and $R^4$, $R^5$ and $R^6$, $R^7$ and $R^8$, when taken together with the carbon to which they are attached, represent carbonyl; or $R^1$ and $R^5$, or $R^1$ and $R^7$, or $R^3$ and $R^5$, or $R^3$ and $R^7$, when taken together form a bridging group —$(CR^{12}R^{13})_n$—, in which n is 1, 2 or 3, and $R^{12}$ and $R^{13}$ are independently hydrogen or lower alkyl; with the proviso that the maximum number of carbonyl groups is 2; the maximum number of —$C(O)NR^9R^{10}$ groups is 1; and the maximum number of bridging groups is 1;

T is oxygen, sulfur, or $NR^{11}$, in which $R^{11}$ is hydrogen or lower alkyl;

V is —N<, —CH<, or —N—CH<;

$X^1$ is hydrogen, optionally substituted lower alkyl, optionally substituted cycloalkyl, optionally substituted aryl, or optionally substituted heteroaryl;

$X^2$ is optionally substituted aryl or optionally substituted heteroaryl;

Y is optionally substituted monocyclic heteroaryl; and $Z^1$ and $Z^2$ are independently optionally substituted alkylene of 1-4 carbon atoms.

A twenty-fifth aspect of this invention is a method of lowering total cholesterol plasma level in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor of Formula II is 1-{4-[5-(4-trifluoromethylphenyl))-[1,2,4]-oxadiazol-3-ylmethyl]-piperazin-1-yl}-3-(2-methylbenzothiazol-1,5-yloxy)-propan-2-ol; as a racemic mixture, or an isomer thereof.

A twenty-sixth aspect of this invention is a method for delaying onset of diabetic retinopathy in a mammal, wherein the mammal is diabetic, non-diabetic, or pre-diabetic, comprising administration of a therapeutically effective amount of a partial fatty acid oxidation inhibitor to a mammal in need thereof.

A twenty-seventh aspect of this invention is a method for delaying onset of diabetic retinopathy in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor is a compound Formula I:

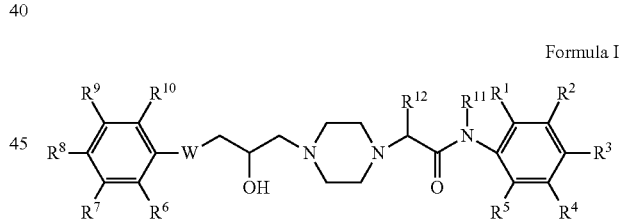

Formula I wherein:

$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, or N-optionally substituted alkylamido, provided that when $R^1$ is methyl, $R^4$ is not methyl;

or $R^2$ and $R^3$ together form —$OCH_2O$—;

$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, or di-lower alkyl amino; or $R^6$ and $R^7$ together form —CH=CH—CH=CH—; or $R^7$ and $R^8$ together form —O—$CH_2O$—;

$R^{11}$ and $R^{12}$ are each independently hydrogen or lower alkyl; and

W is oxygen or sulfur;

or a pharmaceutically acceptable salt or ester thereof, or an isomer thereof.

A twenty-eighth aspect of this invention is a method for delaying onset of diabetic retinopathy in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor is ranolazine, which is named N-(2,6-dimethylphenyl)-4-[2-hydroxy-3-(2-methoxyphenoxy)propyl]-1-piperazineacetamide, as a racemic mixture, or an isomer thereof, or a pharmaceutically acceptable salt thereof.

A twenty-ninth aspect of this invention is a method for delaying onset of diabetic retinopathy in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor is a compound of Formula II:

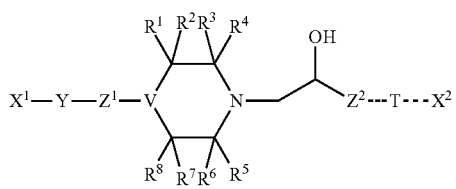

Formula II wherein:
$R^1$, $R^2$, $R^3$, $R^4$, $R^5$, $R^6$, $R^7$, and $R^8$ are hydrogen, lower alkyl, or —C(O)R;
in which R is —OR$^9$ or —NR$^9$R$^{10}$, where $R^9$ and $R^{10}$ are hydrogen or lower alkyl; or
$R^1$ and $R^2$, $R^3$ and $R^4$, $R^5$ and $R^6$, $R^7$ and $R^8$, when taken together with the carbon to which they are attached, represent carbonyl; or
$R^1$ and $R^5$, or $R^1$ and $R^7$, or $R^3$ and $R^5$, or $R^3$ and $R^7$, when taken together form a bridging group —(CR$^{12}$R$^{13}$)$_n$—, in which n is 1, 2 or 3, and $R^{12}$ and $R^{13}$ are independently hydrogen or lower alkyl; with the proviso that the maximum number of carbonyl groups is 2; the maximum number of —C(O)NR$^9$R$^{10}$ groups is 1; and the maximum number of bridging groups is 1;
T is oxygen, sulfur, or NR$^{11}$, in which R$^{11}$ is hydrogen or lower alkyl;
V is —N<, —CH<, or —N—CH<;
$X^1$ is hydrogen, optionally substituted lower alkyl, optionally substituted cycloalkyl, optionally substituted aryl, or optionally substituted heteroaryl;
$X^2$ is optionally substituted aryl or optionally substituted heteroaryl;
Y is optionally substituted monocyclic heteroaryl; and
$Z^1$ and $Z^2$ are independently optionally substituted alkylene of 1-4 carbon atoms.

A thirtieth aspect of this invention is a method for delaying onset of diabetic retinopathy in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor of Formula II is 1-{4-[5-(4-trifluoromethylphenyl))-[1,2,4]-oxadiazol-3-ylmethyl]-piperazin-1-yl}-3-(2-methylbenzothiazol-1,5-yloxy)-propan-2-ol; as a racemic mixture, or an isomer thereof.

A thirty-first aspect of this invention is a method of raising HDL cholesterol plasma level in a mammal, wherein the mammal is diabetic, non-diabetic, or pre-diabetic, comprising administration of a therapeutically effective amount of a partial fatty acid oxidation inhibitor to a mammal in need thereof.

A thirty-second aspect of this invention is a method of raising HDL cholesterol plasma level in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor is a compound Formula I:

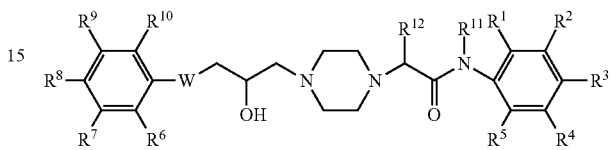

Formula I wherein:
$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, or N-optionally substituted alkylamido, provided that when $R^1$ is methyl, $R^4$ is not methyl;
or $R^2$ and $R^3$ together form —OCH$_2$O—;
$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfonyl, lower alkyl sulfonyl, or di-lower alkyl amino; or
$R^6$ and $R^7$ together form —CH═CH—CH═CH—; or
$R^7$ and $R^8$ together form —O—CH$_2$O—;
$R^{11}$ and $R^{12}$ are each independently hydrogen or lower alkyl; and
W is oxygen or sulfur;
or a pharmaceutically acceptable salt or ester thereof, or an isomer thereof.

A thirty-third aspect of this invention is a method of raising HDL cholesterol plasma level in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor is ranolazine, which is named N-(2,6-dimethylphenyl)-4-[2-hydroxy-3-(2-methoxyphenoxy)propyl]-1-piperazineacetamide, as a racemic mixture, or an isomer thereof, or a pharmaceutically acceptable salt thereof.

A thirty-fourth aspect of this invention is a method of raising HDL cholesterol plasma level in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor is a compound of Formula II:

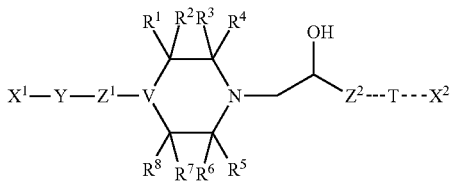

Formula II wherein:
$R^1$, $R^2$, $R^3$, $R^4$, $R^5$, $R^6$, $R^7$, and $R^8$ are hydrogen, lower alkyl, or —C(O)R;

in which R is —OR$^9$ or —NR$^9$R$^{10}$, where R$^9$ and R$^{10}$ are hydrogen or lower alkyl; or R$^1$ and R$^2$, R$^3$ and R$^4$, R$^5$ and R$^6$, R$^7$ and R$^8$, when taken together with the carbon to which they are attached, represent carbonyl; or R$^1$ and R$^5$, or R$^1$ and R$^7$, or R$^3$ and R$^5$, or R$^3$ and R$^7$, when taken together form a bridging group —(CR$^{12}$R$^{13}$)$_n$—, in which n is 1, 2 or 3, and R$^{12}$ and R$^{13}$ are independently hydrogen or lower alkyl; with the proviso that the maximum number of carbonyl groups is 2; the maximum number of —C(O)NR$^9$R$^{10}$ groups is 1; and the maximum number of bridging groups is 1;

T is oxygen, sulfur, or NR$^{11}$, in which R$^{11}$ is hydrogen or lower alkyl;

V is —N<, —CH<, or —N—CH<;

X$^1$ is hydrogen, optionally substituted lower alkyl, optionally substituted cycloalkyl, optionally substituted aryl, or optionally substituted heteroaryl;

X$^2$ is optionally substituted aryl or optionally substituted heteroaryl;

Y is optionally substituted monocyclic heteroaryl; and

Z$^1$ and Z$^2$ are independently optionally substituted alkylene of 1-4 carbon atoms.

A thirty-fifth aspect of this invention is a method of raising HDL cholesterol plasma level in a mammal, wherein the mammal is diabetic, non-diabetic, or pre-diabetic, comprising administration of a therapeutically effective amount of a partial fatty acid oxidation inhibitor to a mammal in need thereof, wherein the partial fatty acid oxidation inhibitor of Formula II is 1-{4-[5-(4-trifluoromethylphenyl))-[1,2,4]-oxadiazol-3-ylmethyl]-piperazin-1-yl}-3-(2-methylbenzothiazol-1,5-yloxy)-propan-2-ol; as a racemic mixture, or an isomer thereof.

A thirty-sixth aspect of this invention is a method of treating diabetes mellitus in a mammal, comprising administration of a therapeutically effective amount of a partial fatty acid oxidation (pfox) inhibitor to a mammal in need thereof, wherein the partial fatty acid oxidation inhibitor is administered as an immediate release formulation.

A thirty-seventh aspect of this invention is a method of treating diabetes mellitus in a mammal, comprising administration of a therapeutically effective amount of a partial fatty acid oxidation (pfox) inhibitor to a mammal in need thereof, wherein the partial fatty acid oxidation inhibitor is administered as a sustained release formulation.

A thirty-eighth aspect of this invention is a method of treating diabetes mellitus in a mammal, comprising administration of a therapeutically effective amount of a partial fatty acid oxidation (pfox) inhibitor to a mammal in need thereof, wherein the partial fatty acid oxidation inhibitor is administered in a formulation that has both immediate release and sustained release aspects.

A thirty-ninth aspect of this invention is a method of treating diabetes mellitus in a mammal, comprising administration of a therapeutically effective amount of a partial fatty acid oxidation (pfox) inhibitor to a mammal in need thereof, wherein the partial fatty acid oxidation inhibitor is ranolazine.

A fortieth aspect of this invention is a method of treating diabetes mellitus in a mammal, comprising administration of a therapeutically effective amount of a partial fatty acid oxidation (pfox) inhibitor to a mammal in need thereof, wherein the sustained in release formulation provides a plasma level of ranolazine between 550 and 7500 ng base/ml over a 24 hour period.

A forty-first aspect of this invention is a method of treating diabetes mellitus in a mammal, comprising administration of a therapeutically effective amount of a partial fatty acid oxidation (pfox) inhibitor to a mammal in need thereof, wherein the sustained release formulation provides a plasma level of ranolazine between 550 and 7500 ng base/ml over a 24 hour period, wherein the sustained release formulation comprises

| Ingredient | Weight Range (%) | A preferred Ranolazine Form'n (mg) |
|---|---|---|
| Ranolazine | 75 | 500 |
| Microcrystalline cellulose (filler) | 10.6 | 70.7 |
| Methacrylic acid copolymer | 10.0 | 66.7 |
| Sodium hydroxide | 0.4 | 2.7 |
| Hydroxypropyl methylcellulose | 2.0 | 13.3 |
| Magnesium stearate | 2.0 | 13.3 |

A forty-second aspect of the invention is a method of treating diabetes mellitus in a mammal comprising administering a compound of Formula I wherein the dosage is from about 250 mg bid to about 2000 mg bid to a mammal A forty-third aspect of this invention is a method of treating diabetes mellitus in a mammal comprising administering from about 250 mg bid to about 2000 mg bid of ranolazine.

A forty-fourth aspect of this invention is a method of reducing negative consequences of diabetes comprising administration of ranolazine.

A forty-fifth aspect of this invention is a method of delaying the onset of diabetes comprising administration of ranolazine.

A forty-sixth aspect of this invention is a method of delaying the initiation of insulin treatment comprising administration of ranolazine.

A forty-seventh aspect of this invention is a method of reducing HbA1c levels in a patient without leading to hypoglycemia comprising administration of ranolazine.

BRIEF DESCRIPTION OF THE FIGURES

FIG. 6. CARISA: Change from Baseline in HbA1c (Dependent vs Non-insulin Dependent Diabetic Patients. This figure shows percentage of HbA1c for both insulin dependent and non-insulin dependent diabetics on placebo, 750 mg ranolazine bid, or 1000 mg ranolazine bid at baseline and at last study value.

DETAILED DESCRIPTION OF THE INVENTION

Figure 1:
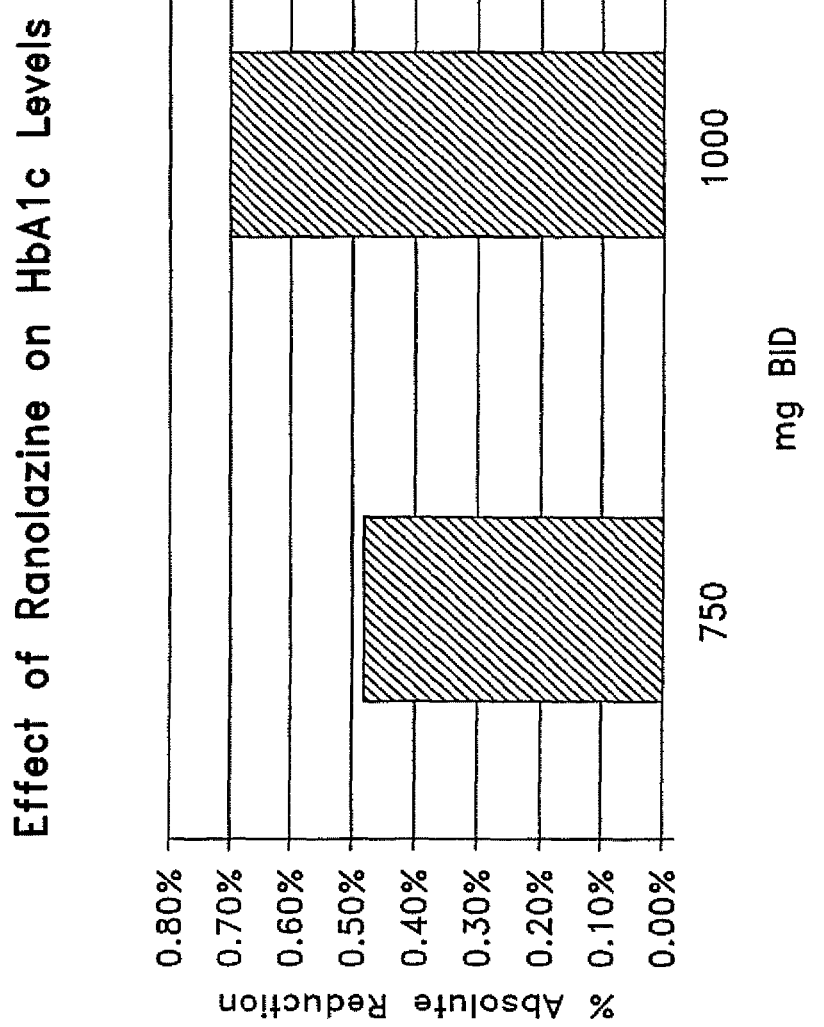
FIG. 1. Effect of Ranolazine on HbA1c Levels.

The invention provides a method of treating diabetes with partial fatty acid oxidation inhibitors, preferably with the compounds of Formula I or Formula II.

Diabetes, as defined herein, is a disease state characterized by hyperglycemia; altered metabolism of lipids, carbohydrates, and proteins; and an increased risk of complications from vascular disease.

Glycemic control is the regulation of blood glucose levels

Hemoglobin undergoes glycosylation on its amino terminal valine residue to form the glucosyl valine adduct of hemoglobin (HbA1c). The toxic effects of hyperglycemia may be the result of accumulation of such nonenzymatically glycosylated products. The covalent reaction of glucose with hemoglobin also provides a convenient method to determine an integrated index of the glycemic state. For example, the half-life of the modified hemoglobin is equal to that of the erythrocyte (about 120 days). Since the amount of glycosylated protein is proportional to the glucose concentration and the time of exposure of the protein to glucose, the concentration of HbA1c in the circulation reflects the glycemic state over an extended period (4 to 12 weeks) prior to sampling. Thus, a rise in HbA1c from 5% to 10% suggests a prolonged doubling of the mean blood glucose concentration With respect to the compound of Formula I, the following words and phrases are generally intended to have the meanings as set forth below, except to the extent that the context in which they are used indicates otherwise.

"Aminocarbonylmethyl" refers to a group having the following structure:

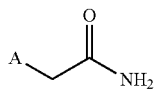

where A represents the point of attachment.

"Halo" or "halogen" refers to fluoro, chloro, bromo or iodo.

"Lower acyl" refers to a group having the following structure:

where R. is lower alkyl as is defined herein, and A represents the point of attachment, and includes such groups as acetyl, propanoyl, n-butanoyl and the like.

"Lower alkyl" refers to an unbranched saturated hydrocarbon chain of 1-4 carbons, such as methyl, ethyl, n-propyl, and n-butyl.

"Lower alkoxy" refers to a group —OR wherein R is lower alkyl as herein defined.

"Lower alkylthio" refers to a group —SR wherein R is lower alkyl as herein defined.

"Lower alkyl sulfinyl" refers to a group of the formula:

wherein R is lower alkyl as herein defined, and A represents the point of attachment.

"Lower alkyl sulfonyl" refers to a group of the formula:

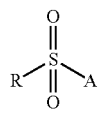

wherein R is lower alkyl as herein defined, and A represents the point of attachment.

"N-Optionally substituted alkylamido" refers to a group having the following structure:

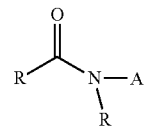

wherein R is independently hydrogen or lower alkyl and R' is lower alkyl as defined herein, and A represents the point of attachment.

With respect to the compound of Formula II, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:
1) an alkyl group as defined above, having from 1 to 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may be optionally further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
2) an alkyl group as defined above that is interrupted by 1-5 atoms or groups independently chosen from oxygen, sulfur and —NR$_a$—, where R$_a$ is chosen from hydrogen, alkyl, cycloalkyl, alkenyl, cycloalkenyl, alkynyl, aryl, heteroaryl and heterocyclyl. Unless otherwise constrained by the definition, all substituents may be optionally further substituted by 1-3 substituents chosen from alkyl, carboxy, carboxyalkyl, amino carbonyl, hydroxy, alkoxy, halogen, CF$_3$, amino, substituted amino, cyano, and —S(O)$_n$R, where R is alkyl, aryl, or heteroaryl and n is 0, 1 or 2; or
3) an alkyl group as defined above that has both from 1 to 5 substituents as defined above and is also interrupted by 1-5 atoms or groups as defined above.

The term "lower alkyl" refers to a monoradical branched or unbranched saturated hydrocarbon chain having from 1 to 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1 to 3 substituents, as defined for substituted alkyl, or a lower alkyl group as defined above that is interrupted by 1-5 atoms as defined for substituted alkyl, or a lower alkyl group as defined above that has both from 1 to 5 substituents as defined above and is also interrupted by 1-5 atoms as defined above.

The term "alkylene" refers to a diradical of a branched or unbranched saturated hydrocarbon chain, preferably having from 1 to 20 carbon atoms, preferably 1-10 carbon atoms, more preferably 1-6 carbon atoms. This term is exemplified by groups such as methylene (—CH2-), ethylene (—CH2CH2-), the propylene isomers (e.g., —CH2CH2CH2- and —CH(CH3)CH2-) and the like.

The term "lower alkylene" refers to a diradical of a branched or unbranched saturated hydrocarbon chain, preferably having from 1 to 6 carbon atoms.

The term "substituted alkylene" refers to:
(1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may be optionally further substituted by 1-3 substituents chosen from alkyl, carboxy, carboxyalkyl, aminocarbonyl, hydroxy, alkoxy, halogen, CF3, amino, substituted amino, cyano, and —S(O)$_n$R, where R is alkyl, aryl, or heteroaryl and n is 0, 1 or 2; or
(2) an alkylene group as defined above that is interrupted by 1-5 atoms or groups independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or
(3) an alkylene group as defined above that has both from 1 to 5 substituents as defined above and is also interrupted by 1-20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1-6, preferably 1, double bond (vinyl). Preferred alkenyl groups include ethenyl or vinyl (—CH═CH$_2$), 1-propylene or allyl (—CH$_2$CH═CH$_2$), isopropylene (—C(CH$_3$)═CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, SO$_2$-aryl and —SO$_2$-heteroaryl. Unless otherwise constrained by the definition, all substituents may be optionally further substituted by 1-3 substituents chosen from alkyl, carboxy, carboxyalkyl, aminocarbonyl, hydroxy, alkoxy, halogen, CF3, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynyl groups include ethynyl, (—C≡CH), propargyl (or prop-1-yn-3-yl, —CH$_2$C≡CH), and the like. In the event that alkynyl is attached to nitrogen, the triple bond cannot be alpha to the nitrogen.

The term "substituted alkynyl" refers to an alkynyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may be optionally further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). Unless otherwise constrained by the definition, all substituents may be optionally further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. Unless otherwise constrained by the definition, all substituents may be optionally further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamimo, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may be optionally further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y—Z, in which Y is optionally substituted alkylene and Z is alkenyl, cycloalkenyl, or alkynyl, Unless otherwise constrained by the definition, all substituents may be optionally further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)β-cycloalkyl, where alkyl and cycloalkyl, are as defined herein, and may be optionally further substituted by alkyl, alkenyl, alkynyl, alkoxy, halogen, $CF_3$, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may be optionally further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may be optionally further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2. Such heteroaryl groups can have a single ring (e.g., pyridyl, furyl, oxadiazolyl, oxazolyl, isoxazolyl, pyrazolyl) or multiple condensed rings (e.g., bicyclic heteroaryl groups such as indolizinyl, benzothiazolyl, benzooxazolyl, benzothienyl, and the like). Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroarylene" or "heteroarylenyl" refers to a diradical of a heteroaryl group as defined above. This term is exemplified by groups such as 3,5-[1,2,4]oxadiazolenyl, 2,4-[1,3]oxazolenyl, 2,5-[1,3]oxazolenyl, 3,5-isoxazolylenyl, 3,4-pyrazolenyl, 3,5-pyrazolenyl, and the like. For example, 3,5-[1,2,4]oxadiazolenyl in the context of a compound of Formula I is represented as:

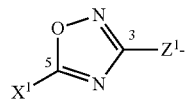

Unless otherwise constrained by the definition for the heteroaryl or heteroarylene substituent, such heterarylene groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may be optionally further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, and prodrugs of such compounds.

"Isomers" refers to compounds having the same atomic mass and atomic number but differing in one or more physical or chemical properties. All isomers of the compounds of Formula I are within the scope of the invention.

"Optional" or "optionally" means that the subsequently described event or circumstance may or may not occur, and that the description includes instances where said event or circumstance occurs and instances in which it does not.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

The term "partial fatty acid oxidation inhibitor" refers to a drug or chemical entity that inhibits mitochondrial fatty acid metabolism. Partial fatty acid oxidation inhibitors induce a metabolic shift from fatty acids to glucose/lactates, shifting the amount of energy obtained from the relatively inefficient metabolism of fatty acids to energy generated by the more efficient oxidation of glucose and lactate. "Fatty acid oxidation inhibitors" also refers to compounds that suppress ATP production from the oxidation of fatty acids and consequently stimulate ATP production from the oxidation of glucose and lactate. In the heart, most of the ATP production is acquired through the metabolism of fatty acids. The metabolism of glucose and lactate provides a lesser proportion of ATP. However, the generation of ATP from fatty acids is less efficient with respect to oxygen consumption than the generation of ATP from the oxidation of glucose and lactate. Thus, the use of fatty acid oxidation inhibitors results in more energy production per molecule of oxygen consumed, allowing the heart to be energized more efficiently. Fatty acid oxidation inhibitors are especially useful, therefore, for treating an ischemic environment in which oxygen levels are reduced.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Pharmaceutical Compositions and Administration

The compounds of the invention are usually administered in the form of pharmaceutical compositions. This invention therefore provides pharmaceutical compositions that contain, as the active ingredient, one or more of the compounds of the invention, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of the invention may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. $17^{th}$ Ed. (1985) and "Modern Pharmaceutics", Marcel Dekker, Inc. $3^{rd}$ Ed. (G. S. Banker & C. T. Rhodes, Eds.).

The compounds of the invention may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One preferred mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbie acid, thimerosal, and the like.

Sterile injectable solutions are prepared by incorporating the compound of the invention in the required amount in the appropriate solvent with various other ingredients as enumerated above, as required, followed by filtration and sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formulas I or II. Administration may be via tablet, capsule or enteric-coated tablets, or the like. In making the pharmaceutical compositions that include at least one compound of either Formula I or II, the active ingredient is usually diluted by an excipient and/or enclosed within a carrier such that the formulation can be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; 5,616,345; and WO 0013687. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formulas I or II are effective over a wide dosage range and are generally administered in a pharmaceutically effective amount. Preferably, for oral administration, each dosage unit contains from 10 mg to 2 g of a compound of Formulas I or II, more preferably 10 to 1500 mg, more preferably from 10 to 1000 mg, more preferably from 10 to 700 mg, and for parenteral administration, preferably from 10 to 700 mg of a compound of Formulas I or II, more preferably about 50 to 200 mg. It will be understood, however, that the amount of the compound of Formulas I or II actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route, for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure-breathing machine. Solution, suspension, or powder compositions may be administered, preferably orally or nasally, from devices that deliver the formulation in an appropriate manner.

The intravenous formulation of ranolazine is manufactured via an aseptic fill process as follows. In a suitable vessel, the required amount of Dextrose Monohydrate is dissolved in Water for Injection (WFI) at approximately 78% of the final batch weight. With continuous stirring, the required amount of ranolazine free base is added to the dextrose solution. To facilitate the dissolution of ranolazine, the solution pH is adjusted to a target of 3.88-3.92 with 0.1N or 1N Hydrochloric Acid solution. Additionally, 0.1N HCl or 1.0N NaOH may be utilized to make the final adjustment of solution to the target pH of 3.88-3.92. After ranolazine is dissolved, the batch is adjusted to the final weight with WFI. Upon confirmation that the in-process specifications have been met, the ranolazine bulk solution is sterilized by sterile filtration through two 0.2 μm sterile filters. Subsequently, the sterile ranolazine bulk solution is aseptically filled into sterile glass vials and aseptically stoppered with sterile stoppers. The stoppered vials are then sealed with clean flip-top aluminum seals.

Compounds of the invention may be impregnated into a stent by diffusion, for example, or coated onto the stent such as in a gel form, for example, using procedures known to one of skill in the art in light of the present disclosure.

In one embodiment, the preferred compositions of the invention are formulated so as to provide quick, sustained or delayed release of the active ingredient after administration to the patient, especially sustained release formulations. The most preferred compound of the invention is ranolazine, which is named (±)-N-(2,6-dimethylphenyl)-4-[2-hydroxy-3-(2 methoxyphenoxy) propyl]-1-piperazine-acetamide, or its isomers, or its pharmaceutically effective salts. Unless otherwise stated, the ranolazine plasma concentrations used in the specification and examples refer to ranolazine free base.

The preferred sustained release formulations of this invention are preferably in the form of a compressed tablet comprising an intimate mixture of compound and a partially neutralized pH-dependent binder that controls the rate of dissolution in aqueous media across the range of pH in the stomach (typically approximately 2) and in the intestine (typically approximately about 5.5). An example of a sustained release formulation is disclosed in U.S. Pat. Nos. 6,303,607; 6,479,496; 6,369,062; and 6,525,057, the complete disclosures of which are hereby incorporated by reference.

To provide for a sustained release of compound, one or more pH-dependent binders are chosen to control the dissolution profile of the compound so that the formulation releases the drug slowly and continuously as the formulation passed through the stomach and gastrointestinal tract. The dissolution control capacity of the pH-dependent binder(s) is particularly important in a sustained release formulation because a sustained release formulation that contains sufficient compound for twice daily administration may cause untoward side effects if the compound is released too rapidly ("dose-dumping").

Accordingly, the pH-dependent binders suitable for use in this invention are those which inhibit rapid release of drug from a tablet during its residence in the stomach (where the pH is below about 4.5), and which promotes the release of a therapeutic amount of compound from the dosage form in the lower gastrointestinal tract (where the pH is generally greater than about 4.5). Many materials known in the pharmaceutical art as "enteric" binders and coating agents have the desired pH dissolution properties. These include phthalic acid derivatives such as the phthalic acid derivatives of vinyl polymers and copolymers, hydroxyalkyleelluloses, alkylcelluloses, cellulose acetates, hydroxyalkylcellulose acetates, cellulose ethers, alkylcellulose acetates, and the partial esters thereof, and polymers and copolymers of lower alkyl acrylic acids and lower alkyl acrylates, and the partial esters thereof.

Preferred pH-dependent binder materials that can be used in conjunction with the compound to create a sustained release formulation are methacrylic acid copolymers. Methacrylic acid copolymers are copolymers of methacrylic acid with neutral acrylate or methacrylate esters such as ethyl acrylate or methyl methacrylate. A most preferred copolymer is methacrylic acid copolymer, Type C, USP (which is a copolymer of methacrylic acid and ethyl acrylate having between 46.0% and 50.6% methacrylic acid units). Such a copolymer is commercially available, from Röhm Pharma as Eudragit® L 100-55 (as a powder) or L30D-55 (as a 30% dispersion in water). Other pH-dependent binder materials which may be used alone or in combination in a sustained release formulation dosage form include hydroxypropyl cellulose phthalate, hydroxypropyl methylcellulose phthalate, cellulose acetate phthalate, polyvinylacetate phthalate, polyvinylpyrrolidone phthalate, and the like.

One or more pH-independent binders may be in used in sustained release formulations in oral dosage forms. It is to be noted that pH-dependent binders and viscosity enhancing agents such as hydroxypropyl methylcellulose, hydroxypropyl cellulose, methylcellulose, polyvinylpyrrolidone, neutral poly(meth)acrylate esters, and the like, may not themselves provide the required dissolution control provided by the identified pH-dependent binders. The pH-independent binders may be present in the formulation of this invention in an amount ranging from about 1 to about 10 wt %, and preferably in amount ranging from about 1 to about 3 wt % and most preferably about 2.0 wt %.

As shown in Table 1, the preferred compound of the invention, ranolazine, is relatively insoluble in aqueous solutions having a pH above about 6.5, while the solubility begins to increase dramatically below about pH 6.

TABLE 1

| Solution pH | Solubility (mg/mL) | USP Solubility Class |
|---|---|---|
| 4.81 | 161 | Freely Soluble |
| 4.89 | 73.8 | Soluble |
| 4.90 | 76.4 | Soluble |
| 5.04 | 49.4 | Soluble |
| 5.35 | 16.7 | Sparingly Soluble |
| 5.82 | 5.48 | Slightly soluble |
| 6.46 | 1.63 | Slightly soluble |
| 6.73 | 0.83 | Very slightly soluble |
| 7.08 | 0.39 | Very slightly soluble |
| 7.59 (unbuffered water) | 0.24 | Very slightly soluble |
| 7.79 | 0.17 | Very slightly soluble |
| 12.66 | 0.18 | Very slightly soluble |

Increasing the pH-dependent binder content in the formulation decreases the release rate of the sustained release form of the compound from the formulation at pH is below 4.5 typical of the pH found in the stomach. The enteric coating formed by the binder is less soluble and increases the relative release rate above pH 4.5, where the solubility of compound is lower. A proper selection of the pH-dependent binder allows for a quicker release rate of the compound from the formulation above pH 4.5, while greatly affecting the release rate at low pH. Partial neutralization of the binder facilitates the conversion of the binder into a latex like film which forms around the individual granules. Accordingly, the type and the quantity of the pH-dependent binder and amount of the partial neutralization composition are chosen to closely control the rate of dissolution of compound from the formulation.

The dosage forms of this invention should have a quantity of pH-dependent binders sufficient to produce a sustained release formulation from which the release rate of the compound is controlled such that at low pHs (below about 4.5) the rate of dissolution is significantly slowed. In the case of methacrylic acid copolymer, type C, USP (Eudragit® L 100-55), a suitable quantity of pH-dependent binder is between 5% and 15%. The pH dependent binder will typically have from about 1 to about 20% of the binder methacrylic acid carboxyl groups neutralized. However, it is preferred that the degree of neutralization ranges from about 3 to 6%. The sustained release formulation may also contain pharmaceutical excipients intimately admixed with the compound and the pH-dependent binder. Pharmaceutically acceptable excipients may include, for example, pH-independent binders or film-forming agents such as hydroxypropyl methylcellulose, hydroxypropyl cellulose, methylcellulose, polyvinylpyrrolidone, neutral poly(meth)acrylate esters (e.g. the methyl methacrylate/ethyl acrylate copolymers sold under the trademark Eudragit® NE by Röhm Pharma, starch, gelatin, sugars carboxymethyl cellulose, and the like. Other useful pharmaceutical exepients include diluents such as lactose, mannitol, dry starch, microcrystalline cellulose and the like; surface active agents such as polyoxyethylene sorbitan esters, sorbitan esters and the like; and coloring agents and flavoring agents. Lubricants (such as talc and magnesium stearate) and other tableting aids are also optionally present.

The sustained release formulations of this invention have an active compound content of above about 50% by weight to about 95% or more by weight, more preferably between about 70% to about 90% by weight and most preferably from about 70 to about 80% by weight; a pH-dependent binder content of between 5% and 40%, preferably between 5% and 25%, and more preferably between 5% and 15%; with the remainder of the dosage form comprising pH-independent binders, fillers, and other optional excipients.

One particularly preferred sustained release formulations of this invention is shown below in Table 2.

TABLE 2

| Ingredient | Weight Range (%) | Preferred Range (%) | Most Preferred |
|---|---|---|---|
| Active ingredient | 50-95 | 70-90 | 75 |
| Microcrystalline cellulose (filler) | 1-35 | 5-15 | 10.6 |
| Methacrylic acid copolymer | 1-35 | 5-12.5 | 10.0 |
| Sodium hydroxide | 0.1-1.0 | 0.2-0.6 | 0.4 |
| Hydroxypropyl methylcellulose | 0.5-5.0 | 1-3 | 2.0 |
| Magnesium stearate | 0.5-5.0 | 1-3 | 2.0 |

The sustained release formulations of this invention are prepared as follows: compound and pH-dependent binder and any optional excipients are intimately mixed (dry-blended). The dry-blended mixture is then granulated in the presence of an aqueous solution of a strong base that is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl. methylcellulose, cationic methacrylate copolymers (dimethylaminoethyl methacrylate/methyl-butyl methacrylate copolymers— Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg, and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

It has been found that these methods produce sustained release formulations that provide lower peak plasma levels and yet effective plasma concentrations of compound for up to 12 hours and more after administration, when the compound is used as its free base, rather than as the more pharmaceutically common dihydrochloride salt or as another salt or ester. The use of free base affords at least one advantage: The proportion of compound in the tablet can be increased, since the molecular weight of the free base is only 85% that of the dihydrochloride. In this manner, delivery of an effective amount of compound is achieved while limiting the physical size of the dosage unit.

Utility and Testing

The method is effective in the treatment of diabetes.

Activity testing is conducted as described in the Examples below, and by methods apparent to one skilled in the art.

The Examples that follow serve to illustrate this invention. The Examples are intended to in no way limit the scope of this invention, but are provided to show how to make and use the compounds of this invention. In the Examples, all temperatures are in degrees Centigrade.

Examples 1-9 illustrate the preparation of representative pharmaceutical formulations containing a compound of Formulas I or II.

EXAMPLE 1

Hard gelatin capsules containing the following ingredients are prepared:
Quantity

| Ingredient | (mg/capsule) |
|---|---|
| Active Ingredient | 30.0 |
| Starch | 305.0 |
| Magnesium stearate | 5.0 |

The above ingredients are mixed and filled into hard gelatin capsules.

EXAMPLE 2

A tablet formula is prepared using the ingredients below:

| INGREDIENT | (mg/TABLET) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

EXAMPLE 4

Tablets, each containing 30 mg of active ingredient, are prepared as follows:
Quantity

| Ingredient | (mg/tablet) |
|---|---|
| Active Ingredient | 30.0 mg |
| Starch | 45.0 mg |
| Microcrystalline cellulose | 35.0 mg |

-continued

| Ingredient | (mg/tablet) |
|---|---|
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 5

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 6

Suspensions, each containing 50 mg of active ingredient per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 7

A subcutaneous formulation may be prepared as follows:

| Ingredient | Quantity |
|---|---|
| Active Ingredient | 5.0 mg |
| Corn Oil | 1.0 mL |

EXAMPLE 8

An injectable preparation is prepared having the following composition:

| Ingredients | Amount |
|---|---|
| Active ingredient | 2.0 mg/ml |
| Mannitol, USP | 50 mg/ml |
| Gluconic acid, USP | q.s. (pH 5-6) |
| water (distilled, sterile) | q.s. to 1.0 ml |
| Nitrogen Gas, NF | q.s. |

EXAMPLE 9

A topical preparation is prepared having the following composition:

| Ingredients | grams |
|---|---|
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 10

Sustained release tablets containing the following ingredients are prepared:

| Ingredient | Weight Range (%) | A preferred Ranolazine Form'n (mg) |
|---|---|---|
| Ranolazine | 75 | 500 |
| Microcrystalline cellulose (filler) | 10.6 | 70.7 |
| Methacrylic acid copolymer | 10.0 | 66.7 |
| Sodium hydroxide | 0.4 | 2.7 |
| Hydroxypropyl methylcellulose | 2.0 | 13.3 |
| Magnesium stearate | 2.0 | 13.3 |

Compound and pH-dependent binder and any optional excipients are intimately mixed (dry-blended). The dry-blended mixture is then granulated in the presence of an aqueous solution of a strong base that is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl. methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg, and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 11

Hemoglobin A1c Assays

HbA1c levels were assayed following a modification of the method of Phillipov (Components of total measurement error for hemoglobin A1c determination. Phillipov, G., et al. Clin. Chem. (2001), 47(10):1851). (see FIG. 1)

EXAMPLE 12

Triglyceride Levels

Test compounds, dissolved in DMSO and suspended in 0.5% tylose, are administered perorally by means of a pharyngeal tube to Syrian gold hamsters. To determine the CETP activity, blood samples (approximately 250 mu.l) are taken by retro-orbital puncture prior to the start of the experiment. The compounds are subsequently administered perorally using a pharyngeal tube. Identical volumes of solvent without compounds are administered to the control animals. Subsequently, the animals are fasted. Then at various times, up to 24 hours after administration of the compounds, blood samples are taken by puncture of the retro-orbital venous plexus.

The blood samples are coagulated by incubation at 4° C. overnight. The samples are centrifuged at 6000 X.g for 10 minutes. The concentration of cholesterol and triglycerides in the resulting serum are determined using modifications of commercially available enzyme tests (cholesterol enzymatic 14366 Merck, triglycerides 14364 Merck).

EXAMPLE 13

In order to study the anti-diabetic actions of the compounds, insulin-dependent diabetes mellitus can be induced by chemical destruction of the pancreas with an i.v. injection of STZ (60 mg/kg, controls can be given saline vehicle). The volume of the injection is equivalent to 0.1 ml/100 g body weight. The injection is delivered into the pre-cannulated jugular vein of young (190-220 g) male Sprague Dawley rats (see below for procedure). At the same time osmotic mini pumps are implanted subcutaneously (see below for procedure) to deliver drugs at a constant rate over the course of the study. Depending on the length of the study, a second mini pump may need to be implanted.

In order to confirm the diabetic state, animals have a blood sample taken from the tail (snip the end off the tail) and their blood glucose determined. Animals with blood glucose levels exceeding 13 mM are considered diabetic and randomized into 4 groups. Two groups receive insulin injections subcutaneously daily to achieve partial glucose control (fasting glucose levels approximately 50% of uncontrolled diabetic animals). One of the partially controlled diabetic groups is treated with the test compound. In addition, two non-diabetic groups are included, one receives the test compound and one does not. Neither of the non-diabetic groups of rats receive insulin.

On a weekly basis, 500 μL blood samples are taken by retro-orbital eye bleed, in isofluorane-anesthetized animals for determinations of the following: blood glucose, serum non-esterified free fatty acids, serum triglycerides, HbA1c, serum insulin, total cholesterol, HDL cholesterol, and serum concentrations of the test compound. Body weight is also measured weekly.

Once stable HbA1c is reached, the study is terminated. When this is established, animals are cannulated in the carotid artery following aseptic techniques. Blood pressure is measured in anesthetized and awake rats. The next day, an oral glucose tolerance test is performed. An oral glucose tolerance test involves administering 1 g glucose/kg by gavage.

Arterial blood samples (0.3 ml) are collected through the jugular catheter that was previously used for measuring blood pressure, prior to and at 10, 20, 30, and 60 min following the glucose challenge and the plasma separated for glucose and insulin assays.

Induction of STZ-Diabetes and Implantation of Osmotic Mini Pumps

Under isofluorane anesthesia, the tail of rats are cleaned with warm water followed by ethanol. A tail vein injection of either STZ or saline is made under anesthesia, using sterile needles and syringe and filter-sterilized solutions. Following i.v. injection, the area has pressure applied to prevent bleeding, and the animal is placed in a clean cage with sterile bedding. In addition to the STZ or saline injection, at the initial time of anesthesia, rats have mini-pumps implanted subcutaneously in the neck region. If the study proceeds beyond 4-weeks, a second implantation is performed. Basically, a small area of the neck is shaved and cleaned extensively with an iodine solution, a small 1-cm incision using a scalpel is made in the dermal layer and the pump is inserted aseptically port-first into the Sub-Q space. The incision is then closed with 1-2 surgical staples as required.

Implantation of Carotid Artery Catheter for Measurement of Blood Pressure and Implementation of Oral Glucose Tolerance Test.

Following conditions using sterile techniques and instruments, an anesthetized rat is laid on its back with the head toward the surgeon and lubricating ointment placed in both eyes. A midline incision is made along the neck to expose the left common carotid artery. A tunnel is made for the catheter using blunt dissection in the subcutaneous pocket on the dorsal section of the neck where it is externalized. Halfcurved forceps are used to isolate the artery and soft plastic tubing passed under the posterior portion of the artery to temporarily impede the blood flow to the isolated area. The anterior portion of the external carotid artery is then ligated with a piece of 4-0 silk suture and light tension is created on the artery by anchoring a pair of hemostats to the ends of the suture material. The external carotid is then semi-transected and a 0.033 or 0.040 mm O.D. catheter inserted and pushed toward the aorta, (around 2-3-cm deep). The catheter is tied in place, secured to the pectoral muscle to prevent removal of the catheter, and the anterior portion of the external carotid permanently ligated and observed for any leakage of blood. Externally, the catheter is tied at the back of the neck and a piece of suture tied around the knot leaving both ends about 2 inches long for retrieval from under the skin. The knotted catheter is retracted back under the skin to prevent being pulled out by the rat. For blood pressure measurements, the catheter is attached to a pressure transducer and a data-acquisition system. For blood glucose tolerance testing, the catheter is attached to a needle and syringe for collection of blood samples.

EXAMPLE 14

In order to study the anti-diabetic actions of the compounds, insulin-dependent diabetes mellitus are induced by chemical destruction of the pancreas with an i.v. injection of STZ (60 mg/kg, controls are given saline vehicle). The volume of the injection is equivalent to 0.1 ml/100 g body weight. The injection is delivered into the pre-cannulated jugular vein of young (280-300 g) male Sprague Dawley rats with 2 catheters surgically implanted in the jugular vein and external carotid artery. In order to confirm the diabetic state, animals have a blood sample taken from the cannula and their blood glucose is determined. Animals with blood glucose levels exceeding 13 mM are considered diabetic. The pre-implanted catheter is flushed daily with heparinized saline to maintain patency. One week after the induction of diabetes, rats undergo pharmacokinetic studies with the compounds of the invention. Animals have their catheters retrieved from under the skin and tested for patency. An injection plug is attached to a 19-gauge IV set, filled with 0.1% heparinized saline and the needle end inserted into the catheters. The test compound(s) is (are) administered via the jugular vein catheter either by bolus injection or steady infusion, or by oral gavage (1 ml/kg and 2 ml/kg, respectively). At 10 time points using 5-6 animals, 300 µl of blood is drawn from the line in the carotid artery and 300 µl saline flushed in to replace blood volume. 300 µl of blood at 10 time points from a 300 gm animal represents ~10% total blood volume. If a 24-hour sample is drawn, the catheters are tied off at skin level and the animals returned to their cages. They are then sacrificed at 24 hours by exanguination under anesthesia to collect the last blood sample. If there is no 24-hour sample, the animals are sacrificed by exanguination under anesthesia at the last blood collection.

EXAMPLE 15

Exercise Performance and Hemoglobin A1c in Angina Patients with Diabetes

The CARISA (Combination Assessment of Ranolazine in Stable Angina) study randomized 823 symptomatic chronic angina patients on diltiazem, atenolol or amlodipine to ranolazine 750 mg bid, 1000 mg bid or placebo in a parallel, double-blind, 12 week study. Modified Bruce treadmill tests were performed at baseline, and after 2, 6, and 12 weeks of treatment at trough and peak plasma levels. The ranolazine formulation used in this study was that shown in Example 10.

Figure 2:
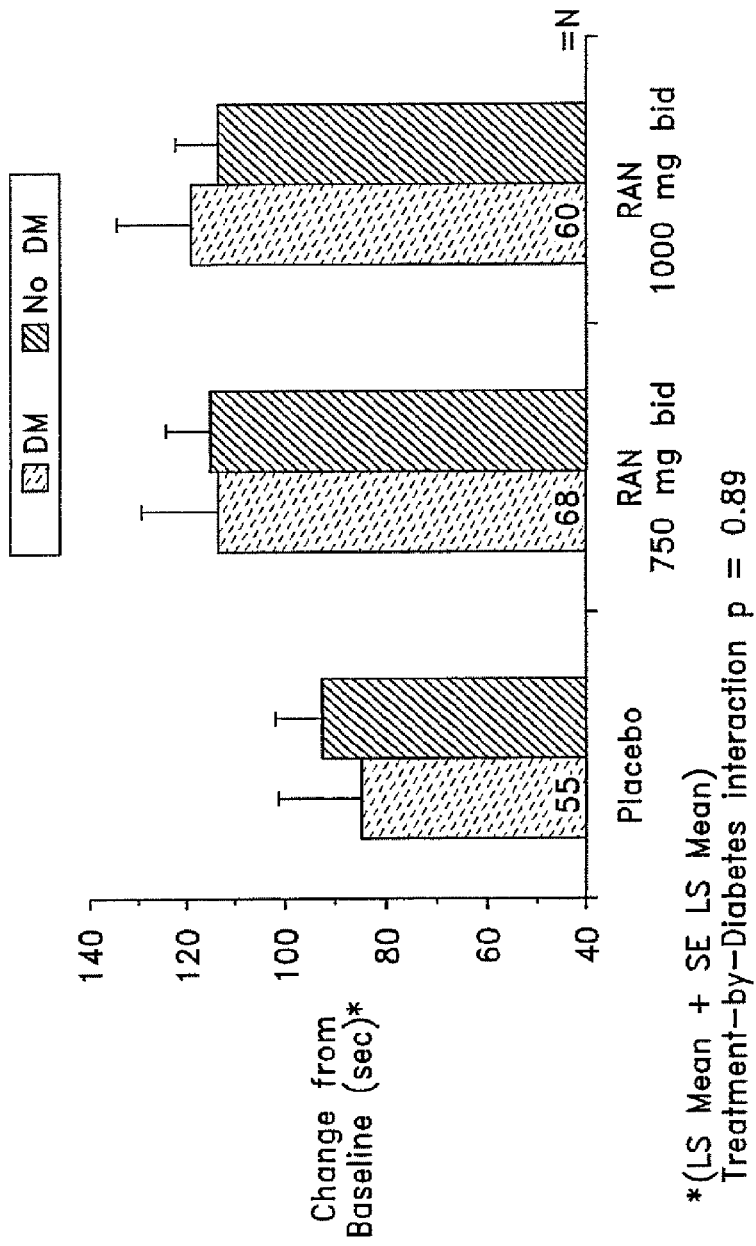
FIG. 2. CARISA Primary Endpoint: Exercise Duration at Trough. This figure shows changes from baseline (in sec) for diabetics and non-diabetics on placebo, 750 mg ranolazine bid, or 1000 mg ranolazine bid.
Figure 3:
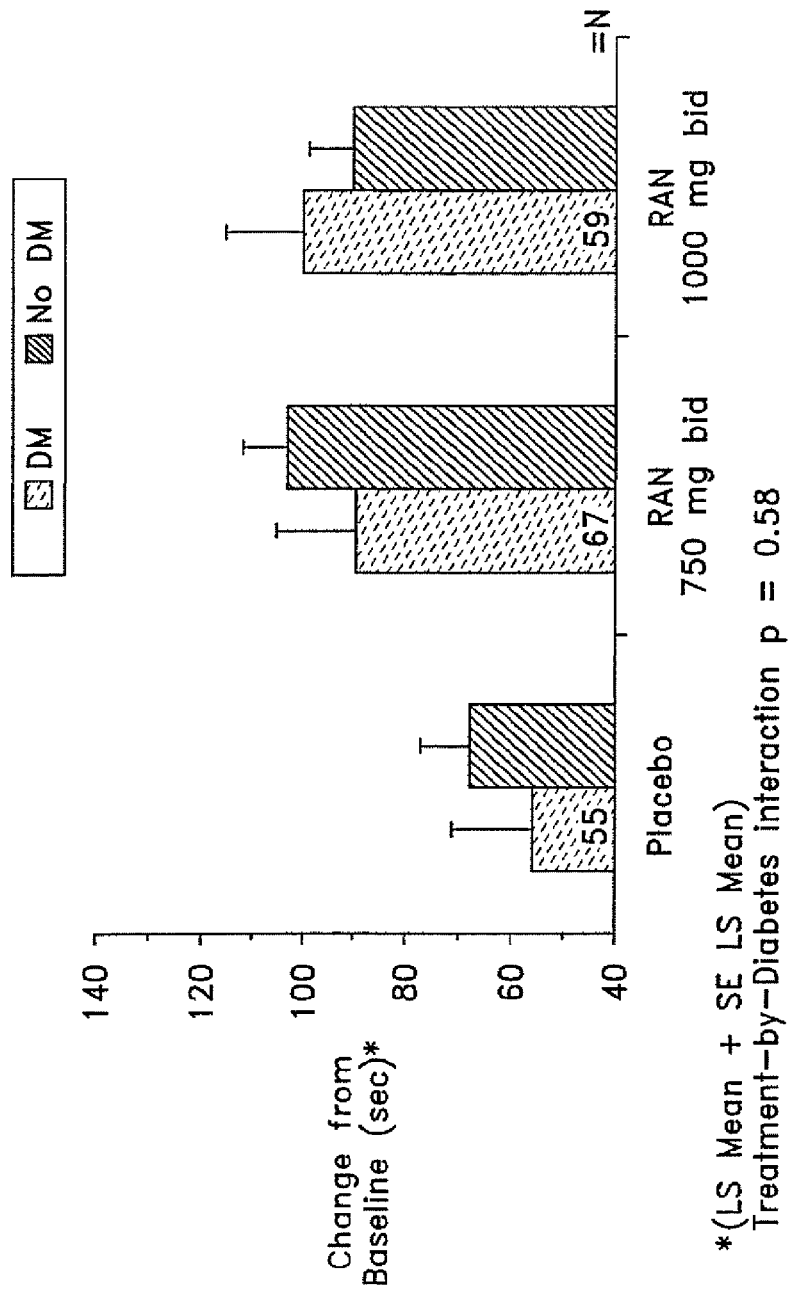
FIG. 3. CARISA: Exercise Duration at Peak. This figure shows changes from baseline (in sec) for diabetics and non-diabetics on placebo, 750 mg ranolazine bid, or 1000 mg ranolazine bid.

Ranolazine prolonged exercise duration (ED) similarly in both diabetic (D) and non-diabetic (ND) patients at trough (FIG. 2) and peak (FIG. 3). The 750 mg dose of ranolazine prolonged exercise duration at trough drug concentrations by 29 seconds in angina patients with diabetes and by 22 seconds in non-diabetic angina patients. The 1000 mg dose of ranolazine prolonged exercise duration at trough drug concentrations by 34 seconds in angina patients with diabetes and by 21 seconds in non-diabetic angina patients.

Figure 4:
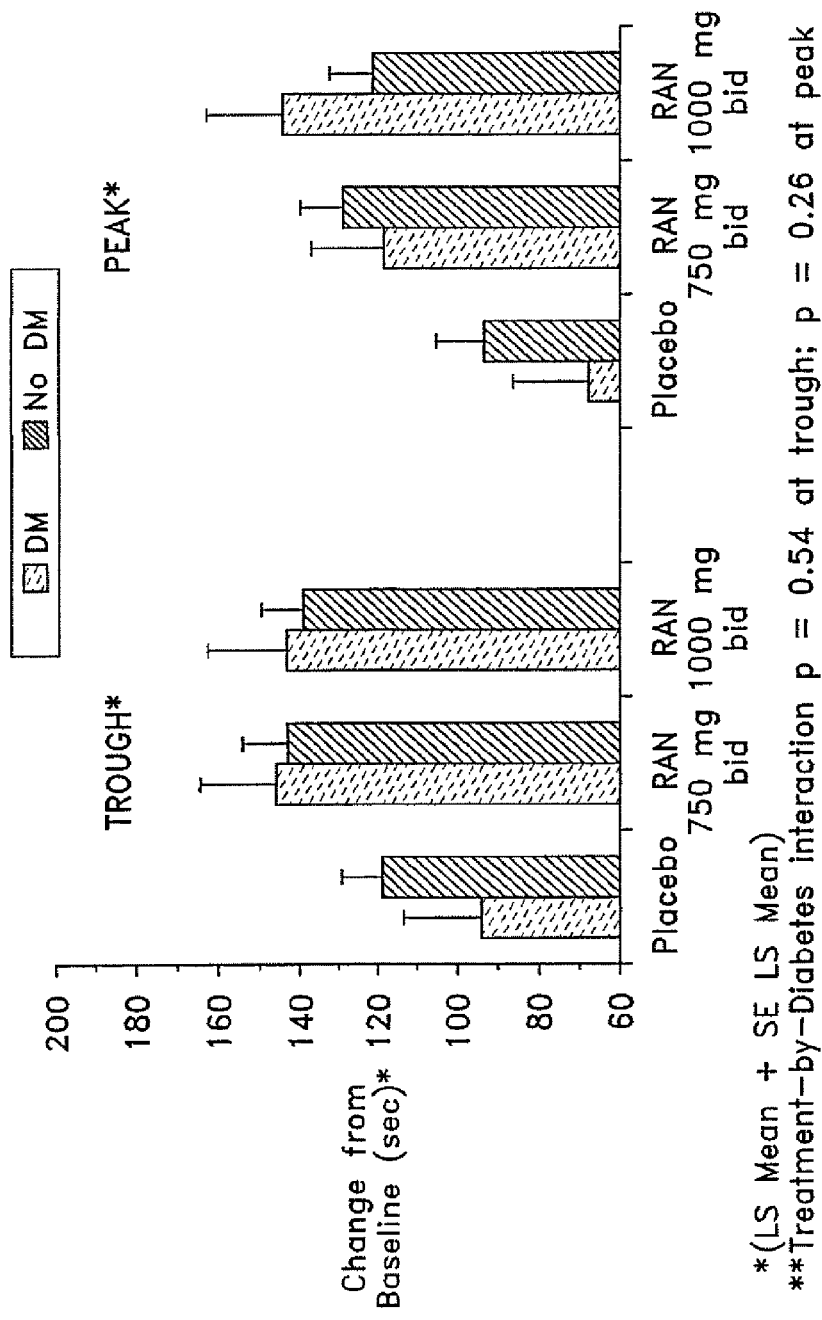
FIG. 4. CARISA: Exercise Time to Onset of Angina. This figure shows changes from baseline (in sec) in trough and peak for diabetics and non-diabetics on placebo, 750 mg ranolazine bid, or 1000 mg ranolazine bid.

Time to angina increased on ranolazine (FIG. 4) and angina frequency decreased. The improvement with ranolazine was not significantly different in D vs. ND patients (treatment by diabetes interaction p-values ≥0.26). Adverse events were similar: 25%, 25% and 34% of D had at least one adverse event on placebo, ranolazine 750 and 1000 mg respectively vs. 27%, 33%, and 32% in ND patients.

Figure 5:
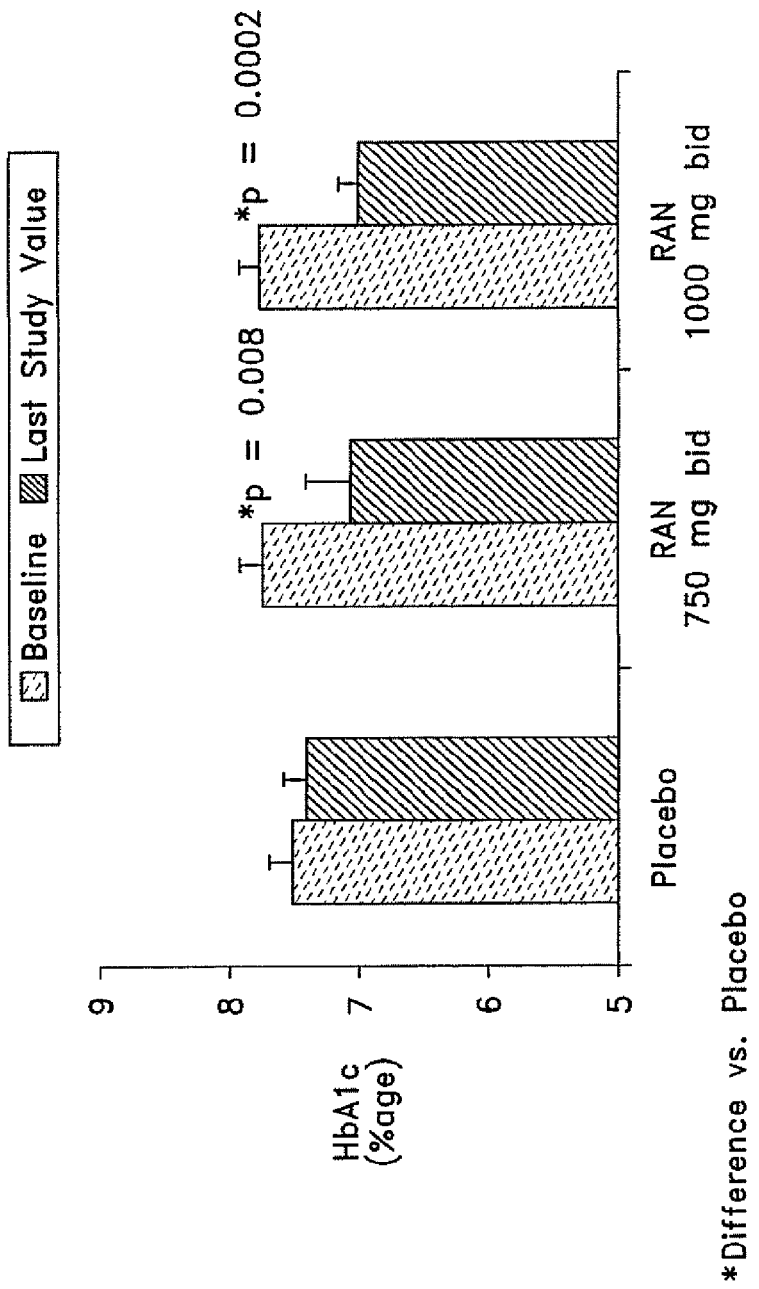
FIG. 5. CARISA: Change from Baseline in HbA1c (all diabetic patients). This figure shows percentage of HbA1c for diabetics on placebo, 750 mg ranolazine bid, or 1000 mg ranolazine bid at baseline and at last study value.

Ranolazine 750 and 1000 mg bid were associated with an average absolute reduction HbA1c of 0.48 percentage points and 0.70 percentage points, respectively compared to placebo at 12 weeks (p<0.01) (FIG. 5). The reductions were greater in those patients on insulin (0.8 and 1.1 percentage points, respectively) (FIG. 6). Glucose and triglyceride values for the diabetic patients in the study are shown in Table 1.

TABLE 1

Glucose and Triglyceride Values (all diabetic patients)

| | Placebo | RAN 750 mg bid | RAN 1000 mg bid |
|---|---|---|---|
| Glucose (mg/dL) | | | |
| Baseline | 177.8 ± 10.8 | 168 ± 8.0 | 165.2 ± 7.8 |
| Change from baseline | 1.2 ± 7.1 | 8.0 ± 8.8 | 1.7 ± 7.2 |
| Triglycerides (mg/dL) | | | |
| Baseline | 233.0 ± 56.8 | 192.0 ± 14.5 | 196 ± 17.5 |
| Change from Baseline | 26.3 ± 21.2 | 21.2 ± 13.5 | −7.3 ± 9.3 |

All values are Mean ± SEM

EXAMPLE 16

Carbohydrate and Lipid Parameters in MARISA and CARISA

Ranolazine (RAN), a member of a new class of drugs that partially inhibits fatty acid oxidation (pFOX), increased treadmill exercise capacity in patients with chronic angina both alone (MARISA, N=191) and when added to background anti-anginal therapy with atenolol, diltiazem, or amlodipine (CARISA, N=823). Angina frequency and nitroglycerin consumption were reduced by ranolazine. The ranolazine formulation used in the CARISA and MARISA studies was that shown in Example 10. The most frequently reported adverse events (dizziness constipation and nausea) were generally mild and occurred in fewer than 10% of patients. The potential use of ranolazine in diabetics is of interest because approximately one in four angina patients has diabetes.

Efficacy and tolerability of ranolazine were similar in both diabetic and non-diabetic patients in both MARISA and CARISA. In diabetic patients in CARISA (N=131), ranolazine 750 and 1000 mg bid were associated with a mean absolute reduction in HbA1c of 0.48 percentage points and 0.70 percentage points, respectively, compared to placebo at 12 weeks (each p<0.01). The reductions versus placebo were greater in those patients on insulin (N=31; 0.84 and 1.05 percentage points), on 750 and 1000 mg bid (p<0.02 and p<0.01), respectively. Fasting glucose was not affected by ranolazine in diabetic patients in CARISA, regardless of insulin treatment; one hypoglycemic episode was reported on placebo and one on ranolazine. After 12-24 months of open-label treatment, HbA1c decreased from baseline in the diabetic patients by 1.1 percentage points. During the first 12 weeks of ranolazine treatment of diabetic patients in CARISA, mean total and LDL cholesterol increased by up to 16 and 11 mg/dL, respectively; however, because of mean increases in HDL cholesterol up to 5 mg/dL, the HDL/LDL ratio changed little. Over 3 years of open-label treatment in the combined MARISA/CARISA diabetic population, total and LDL cholesterol decreased from baseline, while HDL cholesterol continued to increase.

What is claimed is:

1. A method of treating diabetes in a human patient in need thereof, comprising administering to the patient a therapeutically effective amount of ranolazine, as a racemic mixture or a pharmaceutically acceptable salt thereof, and a therapeutically effective amount of an agent selected from the group consisting of sulfonylurea, meglitinide, biguanide, thazolidinedione, alpha glucosidase inhibitor and ACE inhibitor, wherein HbA1c level, as measured after 12 weeks of administration, is reduced in the patient and wherein the patient is not on insulin.

2. The method of claim 1, wherein the biguanide is metformin.

3. The method of claim 1, wherein the patient is non-insulin dependent.

4. The method of claim 1, wherein the HbA1c level is reduced by at least 0.48 percentage point.

* * * * *

UNITED STATES PATENT AND TRADEMARK OFFICE
CERTIFICATE OF CORRECTION

| | | |
|---|---|---|
| PATENT NO. | : 8,883,750 B2 | Page 1 of 1 |
| APPLICATION NO. | : 13/655252 | |
| DATED | : November 11, 2014 | |
| INVENTOR(S) | : Andrew A. Wolff et al. | |

It is certified that error appears in the above-identified patent and that said Letters Patent is hereby corrected as shown below:

IN THE SPECIFICATION

In Column 5, Line 25, please replace "A fourth aspect In a sixth aspect," with --A fourth aspect of--.

In Column 17, Line 41, please replace "R. is lower alkyl" with --R is lower alkyl--.

In Column 31, Lines 35-36, please replace "hydroxypropyl. methylcellulose" with --hydroxypropyl methylcellulose--.

In Column 35, Line 12, please replace "hydroxypropyl. methylcellulose" with --hydroxypropyl methylcellulose--.

Signed and Sealed this
Twenty-second Day of March, 2016

Michelle K. Lee
*Director of the United States Patent and Trademark Office*